US012337149B2

(12) United States Patent
Nemoto et al.

(10) Patent No.: US 12,337,149 B2
(45) Date of Patent: Jun. 24, 2025

(54) INJECTION HEAD AND CHEMICAL INJECTION DEVICE COMPRISING SAME

(71) Applicant: Nemoto Kyorindo Co., Ltd., Tokyo (JP)

(72) Inventors: Shigeru Nemoto, Tokyo (JP); Yumiko Fukikoshi, Tokyo (JP); Toshio Kanetaka, Tokyo (JP); Yasufumi Saitoh, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 41 days.

(21) Appl. No.: 18/182,814

(22) Filed: Mar. 13, 2023

(65) Prior Publication Data

US 2023/0211088 A1 Jul. 6, 2023

Related U.S. Application Data

(62) Division of application No. 16/765,408, filed as application No. PCT/JP2018/043248 on Nov. 22, 2018, now Pat. No. 11,633,544.

(30) Foreign Application Priority Data

Nov. 24, 2017 (JP) ................................ 2017-226350

(51) Int. Cl.
*A61M 5/315* (2006.01)
*A61M 5/00* (2006.01)
*A61M 5/31* (2006.01)

(52) U.S. Cl.
CPC ........ *A61M 5/31511* (2013.01); *A61M 5/007* (2013.01); *A61M 5/31596* (2013.01);
(Continued)

(58) Field of Classification Search
CPC ...... A61M 5/31596; A61M 2005/3125; A61M 2205/505
See application file for complete search history.

(56) References Cited

U.S. PATENT DOCUMENTS 9,675,749 B2* 6/2017 Nemoto ............ A61M 5/14566
2006/0079768 A1* 4/2006 Small ................ A61M 5/14546
600/432

(Continued)

FOREIGN PATENT DOCUMENTS

EP       1 572 266 B1    4/2008
JP       2006-510450 A   3/2006
(Continued)

OTHER PUBLICATIONS

Amendment in Japanese Patent Application No. 2006-510450 A submitted on Nov. 16, 2006.
(Continued)

*Primary Examiner* — Bradley J Osinski
(74) *Attorney, Agent, or Firm* — KNOBBE, MARTENS, OLSON & BEAR, LLP

(57) ABSTRACT

A chemical-liquid injection head including a syringe holding unit which holds a syringe in which a piston member is slidably inserted into a cylinder member having a circular cylindrical shape, a piston driving mechanism having a ram member for moving the piston member of the syringe, and a first light emitting portion which emits light with a first color and illuminates the syringe and a second light emitting portion which emits light with a second color and illuminates the syringe. The first light emitting portion and the second light emitting portion, viewed in a posture at the time of use of the injection head, are provided at an upper side of the ram member.

5 Claims, 26 Drawing Sheets

(52) U.S. Cl.
CPC .............. *A61M 2005/3125* (2013.01); *A61M 2205/505* (2013.01); *A61M 2205/587* (2013.01)

(56) References Cited

U.S. PATENT DOCUMENTS

| | | |
|---|---|---|
| 2007/0250008 A1 | 10/2007 | Gelblum |
| 2011/0137162 A1 | 6/2011 | Bruce et al. |
| 2018/0140778 A1 | 5/2018 | Udagawa et al. |

FOREIGN PATENT DOCUMENTS

| | | |
|---|---|---|
| JP | 2007-229287 A | 9/2007 |
| JP | 5586310 B2 | 9/2014 |
| WO | WO 2004/058332 A2 | 7/2004 |
| WO | WO 2011/125987 A1 | 7/2011 |
| WO | WO 2016/167330 A1 | 10/2016 |
| WO | WO 2016/208611 A1 | 12/2016 |
| WO | WO 2017/040152 A1 | 3/2017 |
| WO | WO 2017/040154 A1 | 3/2017 |

OTHER PUBLICATIONS

Extended European Search Report in European Patent Application No. 18880532.9, mailed Oct. 21, 2021.
International Preliminary Report on Patentability in International Application No. PCT/JP2018/043248 mailed on May 26, 2020.
Office Action in Chinese Application No. 20180087263.7, mailed on Oct. 20, 2021.
Office Action in Japanese Patent Application No. 2019-555373 dated May 23, 2022.
Office Action issued in corresponding Chinese Patent Application No. 201880087263.7, dated Sep. 7, 2022.
Office Action in European Patent Application No. 18 880 532.9 issued on Oct. 8, 2024 in 7 pages.

\* cited by examiner

INJECTION HEAD AND CHEMICAL INJECTION DEVICE COMPRISING SAME

RELATED APPLICATIONS

This application is a divisional of U.S. patent application Ser. No. 16/765,408, filed May 19, 2020, which is the U.S. National Phase under 35 U.S.C. § 371 of International Application No. PCT/JP2018/043248, filed Nov. 22, 2018, designating the U.S., and published in Japanese as WO 2019/103110 on May 31, 2019, which claims priority to Japanese Patent Application No. 2017-226350, filed Nov. 24, 2017, the entire content of which are incorporated herein by reference.

TECHNICAL FIELD

The present invention relates to an injection head and a chemical liquid injector which inject a chemical liquid such as a contrast medium into a patient, and in particular, relates to an injection head and a chemical liquid injector which enable an operator to favorably verify any mixing of air bubbles inside a syringe before injecting.

BACKGROUND ART

As medical imaging diagnosis apparatuses, apparatuses such as CT (Computed Tomography) scanners, MRI (Magnetic Resonance Imaging) apparatuses, PET (Positron Emission Tomography) apparatuses, ultrasonic diagnostic apparatuses, and angiographic imaging apparatuses have been known. At the time of using such imaging apparatuses, a contrast medium, a physiological saline, and the like (hereinafter, simply referred to as 'a chemical liquid') is to be injected into the patient's body.

As an apparatus which injects a chemical liquid automatically, various apparatuses have heretofore been known. Configuration and performance of an apparatus vary according to factors such as a type of a test for which that apparatus is to be used (in other words, a type of imaging apparatus with which that apparatus is to be used), and as a chemical liquid injector for angiography, an apparatus as in Patent Literature 1 has been known. Angiography is a test in which, generally, a thin hollow tube called catheter is introduced inside a blood vessel, and after having a front end of the catheter positioned near an intended portion of the blood vessel, a contrast medium and the like is made to flow through the blood vessel and imaging is carried out. The blood vessels subjected to angiography is projected on a display and the like, and a physician carries out diagnosis and treatment while observing that image. The angiography being a test in which a chemical liquid is injected through a thin catheter, it has a characteristic of an injection pressure becoming extremely high, and this is one of the points at which the chemical liquid injector for angiography differs substantially from a chemical liquid injector for CT examination and a chemical liquid injector for MR examination.

PRIOR ART DOCUMENT

Patent Literature

Patent Literature 1: Japanese Patent No. 5586310

SUMMARY OF THE INVENTION

Problems to be Solved by the Invention

Incidentally, in angiography, it is a general practice to set an empty syringe in a chemical liquid injector, and inject upon sucking a volume of a contrast medium necessary in a hospital. In order that no air bubbles are sent toward the patient while injecting, it is desirable to be able to check favorably an entrainment of air bubbles into the syringe before injecting.

The present invention has been made in view of the abovementioned problem, and an object of the present invention is to provide an injection head and a chemical liquid injector using the same which enable an operator to check favorably the entrainment of air bubbles into the syringe before injection.

Means for Solving the Problems

An injection head according to an aspect of the present invention for solving the abovementioned problems is as follows:

An injection head including
a: a syringe holding unit which holds a syringe, in which a piston member is slidably inserted into a cylinder member having a circular cylindrical shape,
b: a piston driving mechanism having a ram member for moving the piston member of the syringe, and
c: a first light emitting portion which emits light with a first color and illuminates the syringe and a second light emitting portion which emits light with a second color and illuminates the syringe, wherein
the first light emitting portion and the second light emitting portion, viewed in a posture at the time of use of the injection head, are provided at an upper side of the ram member (an upper side of the center point of the ram member when viewed from a front side).

'Posture at the time of use of the injection head' refers to a posture in which a front-end side of the syringe set in the injection head is at a height same as or lower than that of a rear-end side.

Description of Terminology

'Chemical liquid injector' refers to a chemical liquid injector that injects a chemical liquid, and in the present specification, refers to an apparatus which injects at least a contrast medium (particularly a contrast medium used in angiography). The chemical liquid injector may be an apparatus that injects a chemical liquid through a catheter. The chemical liquid injector may include (some of or all of) the following components: One or a plurality of piston driving mechanisms, one or a plurality of control circuits (may be a control unit and the like), one or a plurality of head displays, and one or a plurality of displays. In a case in which, the chemical liquid injector includes components such as an injection head and a console, (a) the injection head may be equipped with a piston driving mechanism and a head display, and the console may be equipped with a control unit and a display. (b) Both the injection head and the console may be provided with a control unit. An injection head in which, a control circuit is disposed at an interior thereof, and another control circuit is disposed even inside the console, is an example of this embodiment.

'Chemical liquid' refers to a liquid such as a contrast medium, a physiological saline, a predetermined medicinal agent, or a mixture thereof.

'Connection'—In the present specification, when it is mentioned that a predetermined instrument and another instrument are connected, it may be in the form of a wired connection or a wireless connection. Moreover, it also includes cases of being connected indirectly via other components, in addition to connections in which the instruments are directly connected to one another.

Specific examples of 'contrast medium' are (i) a contrast medium having an iodine concentration of 240 mg/ml (for example, a viscosity 3.3 mPa·s at 37° C. and a specific gravity 1.268-1.296), (ii) a contrast medium having an iodine concentration of 300 mg/ml (for example, a viscosity 6.1 mPa·s at 37° C. and a specific gravity 1.335-1.371), (iii) a contrast medium having an iodine concentration of 350 mg/ml (for example, a viscosity 10.6 mPa·s at 37° C. and a specific gravity 1.392-1.433), and the like. Note that, a contrast medium having an iodine concentration of 370 mg/ml or higher can also be used.

Specific examples of 'physiological saline' are, a physiological saline (for example, a viscosity 0.9595 mPa·s at 20° C. and a specific gravity 1.004-1.006) in which 180 mg of sodium chloride is contained in 20 mL of a physiological saline, and the like.

Effects of the Invention

According to the present invention, it is possible to provide an injection head and a chemical liquid injector which enable an operator to favorably check any mixing of air bubbles inside a syringe before injecting.

BRIEF DESCRIPTION OF THE DRAWINGS

FIG. 27 is a perspective view showing an example of an installation mechanism of the injection head and the like.

EMBODIMENT FOR CARRYING OUT THE INVENTION

An embodiment of the present invention will be described below by referring to the accompanying diagrams. A specific example of a chemical liquid injector is disclosed below; however, the present invention is not necessarily limited to these specific arrangements.

Figure 1:
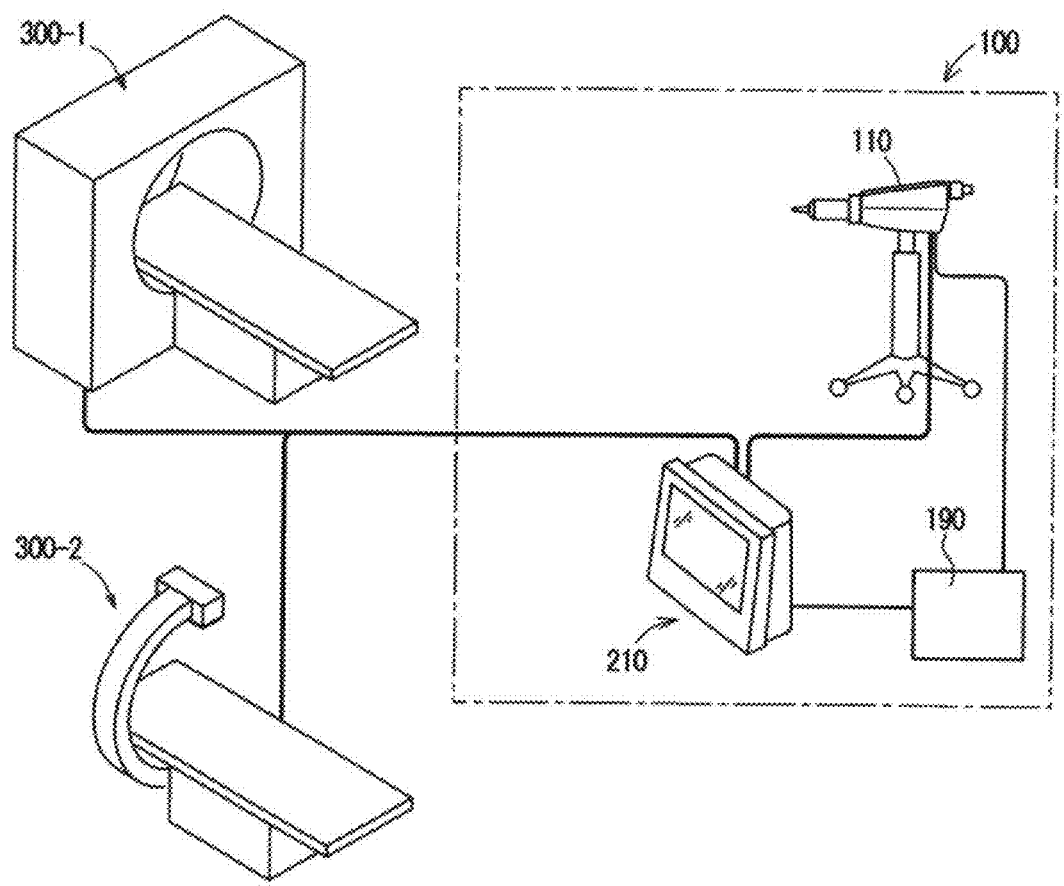
FIG. 1 is a schematic diagram showing a configuration example of a system including a chemical liquid injector of an embodiment of the present invention.

A chemical liquid injector 100 of the present embodiment, as shown in an example in FIG. 1, includes an injection head 110, and a console 210 which is electrically connected to the injection head 10. Moreover, a power-supply unit 190 which supplies an electric power to the injection head 110 and the console 210 may have been provided. In FIG. 1, two imaging apparatuses 300-1 and 300-2 (simply referred to as imaging apparatus 300 as well) are provided. However, there may be only one imaging apparatus. The power-supply unit 190 may be with a built-in control circuit, and the control circuit, for example, is connected to at least one of the injection head and the console, and carries out exchange of signals. Although the chemical liquid injector 100 in FIG. 1 includes three instruments, it may be made of the console 210 and the injection head 110.

As the imaging apparatus 300, for example, an X-ray CT imaging apparatus 300-1 and an imaging apparatus 300-2 for angiography may have been provided. As the imaging apparatus for angiography, it may be an apparatus having a C-arm. The imaging apparatus 300 is tandemly connected to the chemical-liquid injection 100, and exchanges predetermined information mutually. For instance, an arrangement may be made such that timings of a start of operation or an end of operation of one and a start of operation or an end of operation of the other are synchronized.

[1. Syringe for Angiography and Protective Case]

Figure 3:
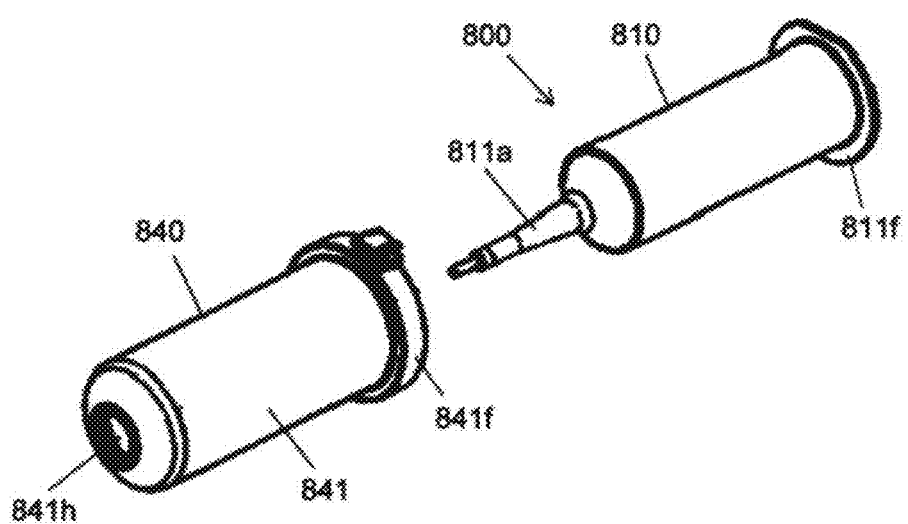
FIG. 3 is a perspective view of a syringe and a protective cover to be put thereon.

Regarding a configuration of a component such as a syringe, a syringe for angiography, and a protective case of the syringe may be as shown in FIG. 3. A syringe 800 (800A and 800B) for angiography has a cylinder member 810 having a circular cylindrical shape and a piston member 820 slidably inserted into the cylinder member 810 (see FIG. 4). A volume of the syringe 800 is not limited and may be either about 50 ml~300 ml or about 100 ml~200 ml for example (in the present specification, 'a~b' is intended for not less than a and not more than b).

A material of the cylinder member 810 may be a material such as a resin, a glass, or a metal. The cylinder member 810 has a flange portion 811f formed on a base-end portion or near the base end portion. An outline shape of the flange portion 811f may be any shape, and it may be a circular shape, an elliptical shape, and a polygonal shape, or may be a shape in which, an outer peripheral portion thereof is cut off partially in a straight line. One or a plurality of notches may be formed in the flange portion 811f, and one notch which is formed as a recess may be formed in each of one side of the flange portion 811f and in an opposite side thereof. A latching mechanism which is not shown but is provided on the injection head is latched in the notch. A thin slender conduit portion (nozzle portion) 811a which is protruded is formed at a front-end portion of the cylinder member 810. A Luer lock structure for connecting a chemical liquid tube is formed at a front end of the conduit portion 811a. The piston member 820 (see FIG. 4) is a plunger of a so-called rodless type, and a latching protrusion 814 to which predetermined rod (not shown) or a ram member of a piston driving mechanism (see FIG. 5 for details) can be joined is formed on a rear surface of the piston member 820.

Note that, generally, a proof pressure of a product has been set in the syringe 800 for angiography. The proof pressure, for example, may be a pressure not lower than 600 psi, a pressure not lower than 800 psi, or a pressure not lower than 1000 psi. The syringe may be of a pre-filled type in which, a chemical liquid (a contrast medium or a physiological saline) has been filled in advance, or of a suction type which is used by sucking the chemical liquid into an empty syringe.

The syringe 800 for angiography is mounted on the injection head 110 in a state of being inserted into a protective case 840 as exemplified in FIG. 3. Such protective case 840, for example, may be a case having a main-body member 841 which is hollow and substantially circular cylindrical shaped. The main-body member 841 has a structure with a front-end side substantially closed and a rear-end side open. The syringe 800 is inserted from an opening on a rear-end side of the protective case 840. An opening portion 841h for passing the conduit portion 811a is formed in a front-end surface of the main-body member 841. A flange portion 841f is formed at a base-end portion of the protective case 840. The flange portion 841f is designed to have a shape and/or strength suitable for being held by a holding structure (for example, clamper mechanism) on the injection head. A material of the protective case 840 is not limited in particular, and may be a material such as a resin, a glass, and a metal.

[2. Injection Head]

Figure 2:
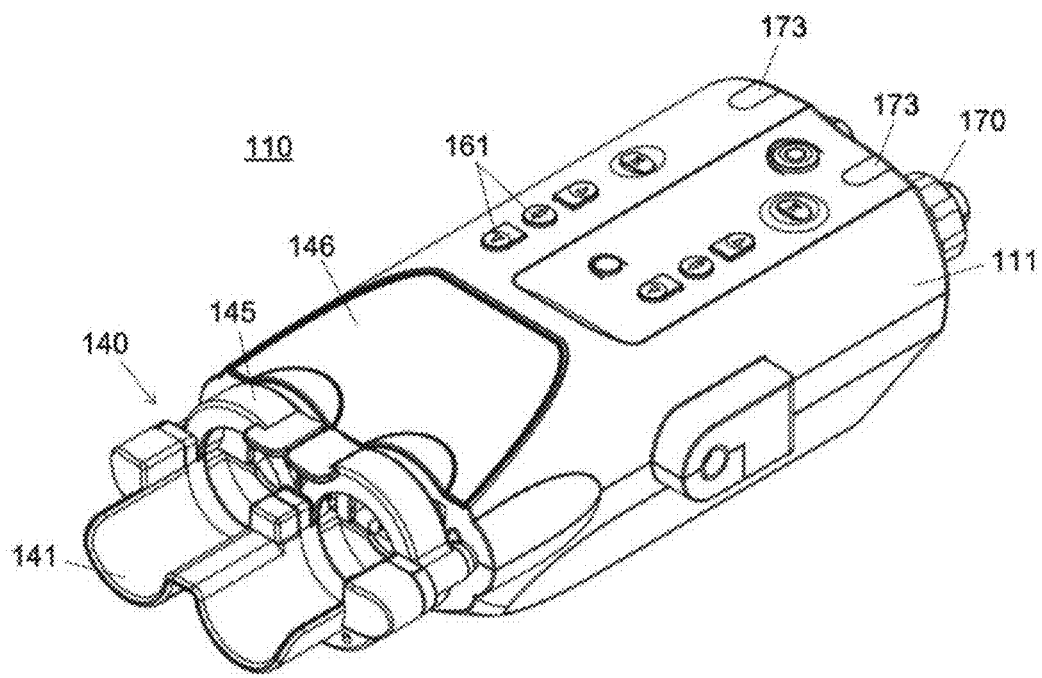
FIG. 2 is a perspective view showing an example of an injection head.

The injection head 110, as shown in FIG. 2, has a housing 111, and the two syringes 800A and 800B (see FIG. 4) are to be mounted on a front-end side of the housing 111. Here, although the description is made with a two-cylinder injection head, the present invention is also applicable to an injection head of a single type which holds a single syringe.

The injection head 110 has a syringe holding unit 140 which holds the syringe 800 in a state of having entered in the protective case 840 (see FIG. 3), a piston driving mechanism 130 (see FIG. 4 and FIG. 5) disposed inside the housing 111, and a control circuit 150 (see FIG. 4) which is electrically connected to the piston driving mechanism 130.

The syringe holding unit 140 has a pair of clampers 145 and a protective case support 141. The clamper 145 is a holding means which holds a portion of the protective case 840. The holding means may be in any form provided that it is capable of holding the protective case 840 stably, and it may be of a type disclosed in Japanese Patent No. 5492873. The protective case support 141 is located on a front-end side of the clamper 145, and has a recess which holds an outer peripheral surface of the protective case 840. The recess, for instance, is formed in a circular arc shape (substantially semicircular) accommodating an outer peripheral surface shape of the protective case 840, and holds a lower side of the protective case 840. The protective case support 141 may be formed of a transparent or a semitransparent material, or, may be formed of an opaque material.

Figure 5:
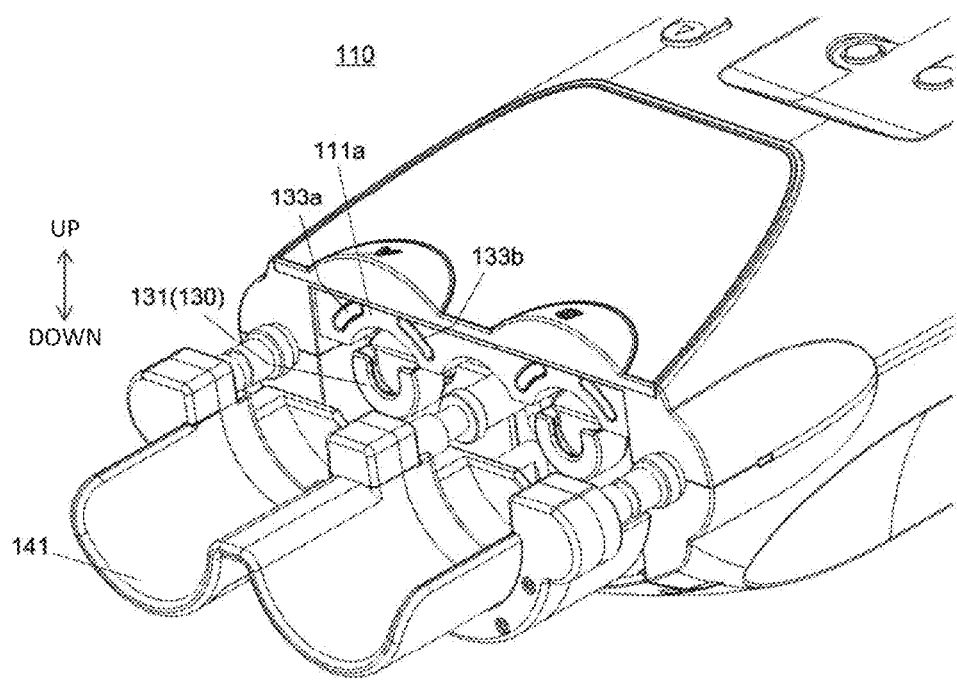
FIG. 5 is a perspective view showing an injection head front-end portion.

The injection head 110 of the present embodiment has been provided with light emitting portions 133a and 133b (also called as light emitting portion 133) at positions shown in FIG. 5. A reference numeral 131 shown in FIG. 5 is a ram member which is a component of the piston driving mechanism, and is a member for slidingly moving the piston member 820 of the syringe. The ram member 131 is a substantial rod-shaped member as a whole, and is designed such that an axis thereof is aligned with a central axis of the syringe 800.

Figure 6:
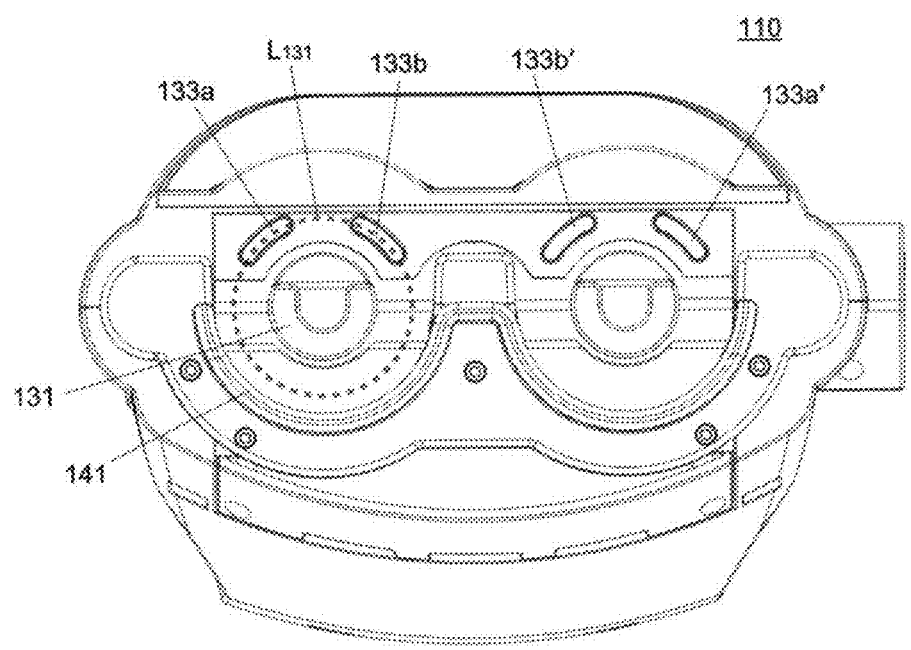
FIG. 6 is a front view showing the injection head front-end portion.

The light emitting portions 133a and 133b are located at a front-end portion of the housing 111 of the injection head 110. Specifically, the light emitting portions 133a and 133b, as shown in FIG. 6, are provided as circular arc shaped opening portions along a reference circle $L_{131}$ which is coaxial with the ram member 131. The circular arc may be formed in a range such that a central angle thereof is 90° or less than 90°, or 60° or less than 60°. An arrangement may be made such that, one light emitting portion 133a emits light with a predetermined color indicating that it is a first chemical liquid (for example, green color as a color indicating that it is a contrast medium), and the other light emitting portion 133b emits light with another color (for example, white color).

Even regarding light emitting portions 133a' and 133b' on the other syringe side, an arrangement may be made such that one light emitting portion 133a' emits light with a predetermined color indicating that it is a second chemical liquid (for example, blue color as a color indicating that it is a physiological saline), and the other light emitting portion 133b' emits light with another color (for example, white color).

As another aspect, the light emitting portion 133a may be let to have a first color (for example, green color) corresponding to a chemical liquid inside the syringe, the light emitting portion 133a' may be let to have a second color (for example, blue color) corresponding to a chemical liquid inside the other syringe, and the light emitting portions 133b and 133b' may be let to be color (third color) other than the two colors. By putting into effect such light emission pattern of three or more than three colors when a specific state is assumed, the operator can check the current state of chemical-liquid injection by looking at that light emission pattern. As a timing, it is not limited in particular, and it may be at a point of time when the standby state has been released.

Other light emission aspects will also be described with the light emitting portions 133a and 133b on a left side illustrated in FIG. 6 as an example. Although an A-syringe side is let to be an example, a B-syringe side may be let to undergo a similar operation. For instance, when the protective case 840 has not been mounted (FIG. 3), the light emitting portions 133a and 133b are not let to emit light. An arrangement may be made such that when the protective case 840 is mounted, one or both of the light emitting portions 133a and 133b are turned on or blinked. Specifically, an arrangement may be made such that the light emitting portion 133b of white light is turned on. It may be a mode of not turning the light emitting portion on, but making it blink. Such switching of light emission, for example, may be carried out with a result of detecting whether or not the protective case 840 is there, as a trigger. Alternatively, the switching may be carried out with a result of detecting whether or not the clamper 145 is open or closed, as a trigger.

As a light emission aspect during chemical-liquid injection, for example, in a case of injection only by the A-syringe out of the A-syringe and the B-syringe, the A-syringe side makes only the light emitting portion 133a (for example, green color) emit light and the B-syringe side makes only the light emitting portion 133b' (for example, white color) emit light (or may not be made to emit light). The light emitting portion 133a may be either turned on or blinked. In a case of injection only by the B-syringe, the A-syringe side makes only the light emitting portion 133b (for example, white color) emit light (or may not be made to emit light), and the B-syringe side makes only the light emitting portion 133a' emit light (for example, blue color). The light emitting portion 133a' may be either turned on or blinked.

As a light emission aspect during chemical-liquid injection, an arrangement may be made such that the side which is injecting is blinked (lit with a color corresponding to a chemical liquid inside the syringe in particular) and the side which is not injecting is turned on (turned on with a color corresponding to a chemical liquid inside the syringe in particular). In case of a protocol in which the chemical liquid of the A-syringe and the chemical liquid of the B-syringe are injected, this aspect may be applied. Next, in a case of a protocol in which only the A-syringe side is injected, the side which is not injecting may be let to blink (lit with a color corresponding to a chemical liquid inside the syringe in particular), and the side which is not injecting may be let to be turned off. In a case of a protocol in which only the B-syringe side is injecting, the side which is not injecting may be let to blink (lit with a color corresponding to a chemical liquid inside the syringe in particular), and the side which is not injecting may be let to be turned on (lit with a color corresponding to (suitable for) a chemical liquid inside the syringe in particular).

In a case of injecting simultaneously by the A-syringe and the B-syringe, only the light emitting portion 133a (for example, green color) and the light emitting portion 133a' (for example, blue color) may be made to emit light, and the light emitting portions 133b and 133b' may not be made to emit light. The light emission at this time may be either by turning on or blinking.

When some kind of error occurs, all the light emitting units may be blinked.

A luminous source of the light emitting portions 133a and 133b is not limited, and an LED (light emitting diode) for instance can be used. A direction of irradiation of the luminous source may be a direction parallel to the central axis of the syringe 800. By illuminating the chemical liquid inside the syringe by the light of the light emitting portions 133a and 133b, the operator is able to carry out visual check of a quantity of the chemical liquid and mixing of air bubbles etc. in the chemical liquid inside the syringe. A size of the reference circle $L_{131}$ (in other words, positions of the light emitting portions 133a and 133b) may be about the same as that of the flange portion 841f of the protective case 840 (see FIG. 3). (in this case, the light is irradiated to the flange portion 841f), or may be a position at an outer side of the flange portion 841f.

As a specific configuration example, a front-end surface 111a of the injection head 110 may be formed as a vertical surface (when the head is let to have a horizontal posture), and the light emitting portions 133a and 133b may be opening portions formed in that vertical surface. For preventing an entry of the chemical liquid, a transparent resin member may have been fitted in the opening portion. Moreover, in order that the transparent resin member does not protrude from or is not caved in the front-end surface 111a, it is preferable to form the transparent resin member on the same plane of the same surface for example.

It is possible to use conventional known configuration for a plurality of structures in the injection head 110, and while the description in detail thereof is omitted, the piston driving mechanism, the control circuit, and various sensors may be as described below.

(Piston Driving Mechanism)

Figure 4:
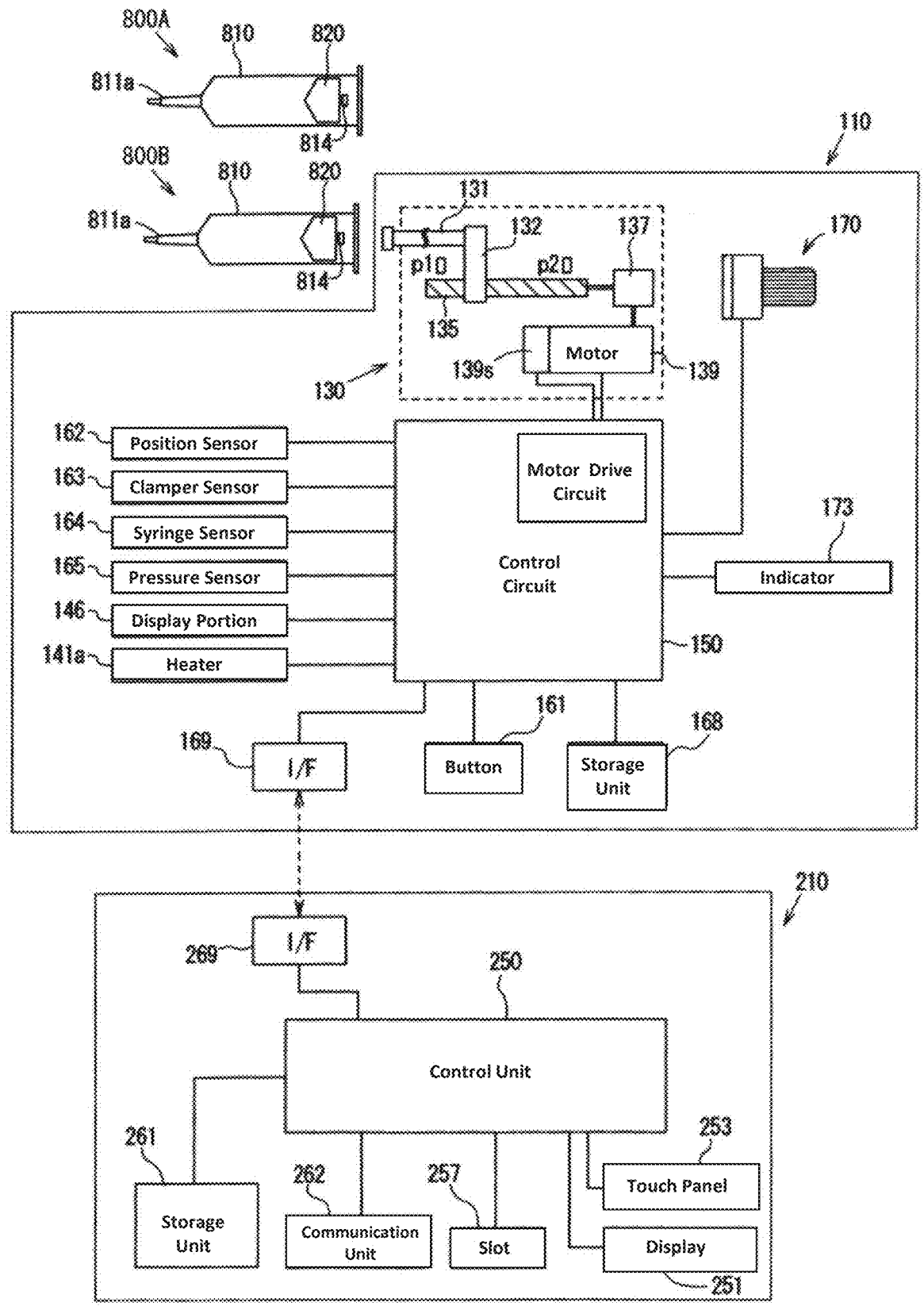
FIG. 4 is a block diagram showing schematically a configuration of components of the chemical liquid injector.

The piston driving mechanism 130, as shown in FIG. 4, includes a motor 139 as an actuator, a transmission mechanism 137 which transmits a rotational output of the motor 139, a ball screw 135 which is rotated by the transmission mechanism 137, a ball nut unit 132, a ram member 131 which moves back and forth with the movement of the ball nut unit 132, and a frame (not shown) which holds at least some of these components. In one embodiment, the ball screw 135 is provided with an encoder (not shown), and an amount of rotation and an angle of rotation can be detected.

As the motor 139, it is possible to use a direct current motor, and among direct current motors, it is possible to use a direct-current brushless motor preferably. A brushless motor, by not having a brush, has an advantage of a low noise and superior durability. Generally, a brushless motor has a sensor for detecting a position of a magnet inside. Therefore, the amount of rotation and a rotational velocity of the motor may be detected by using an output from this sensor. However, a rotation sensor 139s for detecting the amount of rotation and/or the rotational velocity of the motor may have been provided separately. Specifically, it is possible to use a rotary encoder, a resolver, and the like. In angiography, for injecting a contrast medium with a relatively high pressure, it is preferable to use a high-output motor, for example, a motor with an output not less than 70 w, 150 W, not less than 250 W, not less than 300 W, and not less than 400 W.

The output of the motor 130 is transmitted to the ball screw 135 via the transmission mechanism 137. The transmission mechanism 137 may be any transmission mechanism, and as an example, it may be a transmission mechanism having a first pulley (not shown) which is directly or indirectly connected to an output shaft of the motor 139, a second pulley (not shown) which is directly or indirectly connected to the ball screw 135, and a belt (not shown) which is put around these two pulleys. Note that, a gear unit, a chain transmission mechanism, and the like may be used instead of such belt transmission mechanism.

(Description of Block Diagram)

The injection head 110, as shown in FIG. 4, includes for example, the control circuit 150, a storage unit 168, a physical button 161 as an input device, an operation knob 170 as another input device, various sensors 162~165, a display portion 146, a heater 141a, and an indicator 173.

The operation knob 170 may be a knob which is physically linked to a predetermined mechanism inside the housing 111 of the injection head 110, and when the operation knob 170 is rotated, a force thereof may be transmitted to the piston driving mechanism 130, thereby the ram member 131 moving back or forth. Alternatively, the operation knob 170 may be a knob which is not physically linked (contactless) to a predetermined mechanism inside the housing 111, and which detects the rotation electrically, and activates a drive source of the piston driving mechanism 130 by using a detection result thereof, thereby making the ram member 131 move back or forth. In the latter case, for making the operator feel easily the rotating of the operation knob 170, an arrangement such as getting a click corresponding to the rotation may be adopted.

(Control Circuit)

The control circuit 150 includes a CPU (Central Processing Unit) which carries out arithmetic processing, a memory, and an interface, and realizes various functions by executing computer programs stored in the memory. The control circuit 150 may include a processor such as a one-chip microcomputer. The control circuit 150 may have a processor mounted on a predetermined substrate, and various sorts of electric circuits (for example, a motor driving circuit) provided on the substrate. The control circuit 150 is electrically connected to various components of the injection head.

The control circuit 150, for example, may be configured (programmed) to carry out the following processing:

carry out a predetermined arithmetic processing, and control based on signals from various sensors, transmit a predetermined motor control signal to the piston driving mechanism, and control the operation, display predetermined information on the display, receive an input from the operator via the input device such as physical buttons, and control an operation of the heater.

(Various Sensors etc.)

(a1) Position Sensor

A position sensor 162 is for regulating a range of movement of the ram member 131. The position sensor 162, for instance, may have a first sensor which detects that the ram member 131 has moved up to the most advanced position and a second sensor which detects that the ram member 131 has moved up to the most receded position. The first sensor and the second sensor may be contact-type sensors or contactless sensors. As a contactless sensor, it is possible to use an optical sensor having a light emitting element and a light receiving element. Specifically, it may be a photo interrupter which carries out detection by capturing a decrease in an amount of light received by the light receiving element caused due to light being shielded by an object to be detected. Moreover, a reflection-type photo interrupter may be used. The first sensor may be disposed at an anterior side in a direction along a direction of movement of the ram member 131 (see reference numeral p1) and the second sensor may be disposed at a posterior side (see reference numeral p2) as shown schematically in FIG. 4. In addition, as a position sensor, sensors such as a contact sensor using a physical contact, an electric sensor which detects an object electrically, a magnetic sensor, a hall sensor, and a proximity sensor can be used.

(a2) Clamper Sensor

A clamper sensor 163 may be a contact sensor which, when the clamper 145 has closed up to a predetermined closing position, makes a contact with a portion thereof. Alternatively, the clamper sensor 163 may be a contactless sensor which, when the clamper 145 has closed up to a predetermined closing position, detects optically or magnetically a position of the portion thereof.

(a3) Syringe Detection Sensor

A syringe detection sensor 164 is used for detecting whether or not the syringe and/or the protective case have been mounted. Moreover, the syringe detection sensor 164 may be capable of judging as to what type of syringe and/or protective case have/has been mounted. As such sensor, it is possible to use the following sensors which may be one of a contact type or a contactless type: a contact sensor using a physical contact, an electric sensor which detects an object electrically, a magnetic sensor, a hall, sensor, a proximity sensor, and the like.

The various sensors described above can be used not only for the detection of a syringe but also for the detection of a protective case. For instance, the protective case is configured to be provided with one or a plurality of identification members, and the identification member(s) is (are) detected by a sensor. As an identification member, it is possible to use a metal, a magnet, and the like. Identification information may be a size (dimension such as a diameter dimension and/or a length dimension. In other words, as to a syringe of what sort of diameter and/or a syringe of what sort of length it corresponds to) of the protective case, and may include at least one of information such as information of the chemical liquid in the syringe. Information may be identified by detecting a difference of polarity of a magnet. There may be one or a plurality of magnets. A position at which the identification information is to be provided is not limited, and may be the flange portion or vicinity of the flange portion of the protective case. Specifically, one or a plurality of identification members may be provided to a portion protruding from the flange portion. 'The portion protruding from the flange portion' may be a structural part in a substantial plate form, or may be a projected shape of a predetermined length projected toward outer side in a radial direction of the flange portion.

As a specific example, using a plurality of magnets, it is possible to carry out detection by letting it to be detected as a first type when all the magnets are N-pole magnets, as a second type when all the magnets are S-pole magnets, as a third type when one magnet is an N-pole magnet and the other magnet is an S-pole magnet, and as a fourth type when one magnet is an S-pole magnet and the other magnet is an N-pole magnet. In one embodiment, it is preferable that the chemical liquid injector is configured to set automatically the range of movement of the ram member on the basis of information read in such manner. Moreover, the chemical liquid injector may be configured to identify a type and a product name of a chemical liquid, or to identify whether or not it is a prefilled syringe, on the basis of information read in such manner.

(a4) Pressure Sensor

A pressure sensor 165 is for calculating a pressure that pushes the piston member 820 of the syringe, and accordingly, it is possible to calculate an estimated value of pressure of the chemical liquid. The pressure sensor 165, for example, may be a load cell. The load cell is to be provided at a location which enables to detect pressure of the ram member 131 of the piston driving mechanism 130 which pushes the piston member. In a case of calculating the estimated value of pressure of the chemical liquid while injecting the chemical liquid by using a detection result of the load cell, the calculation may be carried out by taking into consideration a size of a needle, a concentration of the chemical liquid, and injection conditions etc. Note that, the calculation of the pressure, apart from by using the pressure sensor as described above, may be carried out on the basis of a motor current of the piston driving mechanism, or such motor current method may be used in combination with the pressure sensor, or may be mounted independently without providing the pressure sensor.

(a5) Display

One or a plurality of display units for displaying predetermined information may be provided to the injection head or may be provided separately from the injection head. The display unit 146 may be an LCD (Liquid Crystal Display) or may be a display using an organic EL (Organic Electro-Luminescence).

Next, content to be displayed on the display unit is not limited in particular, and may be at least one of the following:
  a display related to self-check,
  a predetermined-state display before start of injection,
  a predetermined display related to a posture of the head,
  a predetermined display related to mounting the syringe,
  a predetermined-state display during an injection operation,
  a display of conditions for injecting a chemical liquid scheduled to be injected,
  a display of conditions for injecting a chemical liquid injected,
  a display of a warning in an abnormal case, and the like.

(a6) Heater

In the injection head of the present embodiment, a warming element for warming the chemical liquid in the syringe may be provided, and for example, a transparent heater 141a using an ITO film may be provided.

(a7) Interface

An interface 169 is a connecting unit for carrying out an exchange of signals with the console 210. The connection between the console 210 and the injection head 110 may be a wired connection or a wireless connection.

(a8) Storage Unit

The storage unit 168 may be any type of storage unit provided that it is a storage medium capable of storing data, and can be a memory, a hard disc, and the like. Information (such as operation algorithm) and data table related to a basic operation of the injection head may be stored in the storage unit 168. Some of such information may be stored in a storage unit 261 on the console side and not on the injection-head side.

(a9) Physical Button

The physical button 161 is not limited in particular, and may be as follows.
  a forward button for making the ram member move forward (advance),
  a back off button for moving the ram member backward,
  an accelerator button which accelerates a velocity of movement of the ram member by being pressed simultaneously with the forward button and the back off button,
  return button which returns the ram member up to a receding position,
  a stop button which halts the operation of the head, etc.

(a10) Light Emitting Portion

The indicator 173 in FIG. 4, for example, is an LED (Light Emitting Diode), and is for informing an operation state of the injection head to the operator.

[3. Console]

The console 210, as shown in FIG. 4, may include a control unit 250, a storage unit 261, a communication unit 262, a slot 257, a touch panel 253, and a display 251. For example, the console 210 may be an integrated console in which the control unit 250 is disposed inside one housing, and the display 251 is disposed on a front surface of that housing. It may be a system using not one console, but a plurality of consoles.

A form of the housing is not at all limited. The shape of the housing may be appropriately preferable according to a situation in which the console is to be used. For instance, it may be the following shape:
  a stationary housing shape which is appropriate for using by being disposed on a table in an operation room,
  a housing shape that can be installed preferably on a predetermined supporting member or wall (a thin housing having a rear-surface side formed substantially flat), and the like.

The display of the console may be a display unit in which an LCD (Liquid Crystal Display) and an organic EL (Organic Electro-Luminescence) is used. Moreover, the display may be a touch-panel type display.

The control unit 250 includes a CPU (Central Processing Unit) which carries out arithmetic processing, a memory, and an interface, and realizes various functions by executing computer programs stored in the memory. The control unit 250 may have a processor which has hardware such as a CPU, an ROM, an RAM, and an I/F, and in which, computer programs are installed. The control unit 250 has a large number of functions according to the computer programs that have been installed, and the functions of the console include the following functions:

an injection condition setting GUI display function, an injection condition setting function, a function of screen display during injection, a function of screen display after injection, an input detection function, and an injection control function.

The computer programs may have been stored in advance in the storage unit of the console, or may have been stored in the storage unit upon being downloaded from outside via the network, or may be read from an information storage medium inserted into a slot. The same applies to a computer program which controls the operation of the injection head, and may have been stored in the storage unit of the injection head or the storage unit of the console, or may be read from outside.

Each function mentioned above will be explained briefly. The injection condition setting GUI display function displays a GUI screen for setting the injection conditions, on the display. As a specific example, the injection condition setting GUI display function displays at least one of icons such as a body-segmentation icon, imaging-part icon, and shows predetermined chemical-liquid injection conditions when that icon is selected. The GUI screen in detail will be described later by referring to other diagrams as well.

The injection condition setting function sets contents of check/correction after the chemical-liquid injection conditions shown above are checked/corrected by a physician or a medical staff.

The function of screen display during injection displays still images or animation images during injection of a chemical liquid, on the display. Moreover, the function of screen display during injection displays a pressure of a chemical liquid during injection of the chemical liquid.

The function of screen display after injection displays information related to chemical-liquid injection that has been executed.

The input detection function receives an input from the physician or the medical staff, which is carried out via the touch panel or the physical buttons (for example).

The injection control function activates the piston-driving mechanism according to the input conditions that have been input, and executes the injection of the chemical liquid. It may be configured that information related to conditions for operation of the piston driving mechanism is transmitted to the injection head from the console and the control circuit of the injection head controls the piston driving mechanism on the basis of the information transmitted.

The control unit 250 may further have an injection-history generating function. The injection-history generating function is a function of generating injection-history data. The 'injection-history data' may be one or a plurality of the following for example:

data related to the operation of the heater (heating-start time and heating-end time),
an injection job ID which is unique identification information for each operation job,
date and time of start and end of injection,
identification information of chemical liquid injector,
information of chemical liquid and imaging part that are injection conditions,
information of chemical liquid and injection pressure as injection result.

Referring back to FIG. 4, the slot 257 is a portion into which a predetermined information storage medium is to be inserted, and the console 210 is capable of reading predetermined data from the information storage medium that have been installed.

inserted. An interface 269 is a connecting portion for making connections with the injection head 110. The console 210 may be connectible to an external network (such as a hospital system or the Internet) via the communication unit 262. Although it is not shown in FIG. 4, the console unit 210 may have a hand switch or a foot switch as an inputting means. The hand switch may be connected by wire or by wireless to the console, and operated at hands of the user, or may have a push-button type switch. The operation of the injection head 110 and/or console 210 may be controlled by operating these switches. The foot-switch, in another embodiment, may be connected to the injection head 110. The console may include a speaker (not shown) for outputting a sound and/or voice. The console may include a microphone (not shown) for inputting voice.

[Graphical User Interface]

The chemical liquid injector 100 may have one or a plurality of data of the following screens, and may display that data: a startup-self-check screen, an angiography-mode screen, a home screen, an injection result screen, a protocol setting screen, and an error screen.

(b1: Screen Transition)

Figure 7:
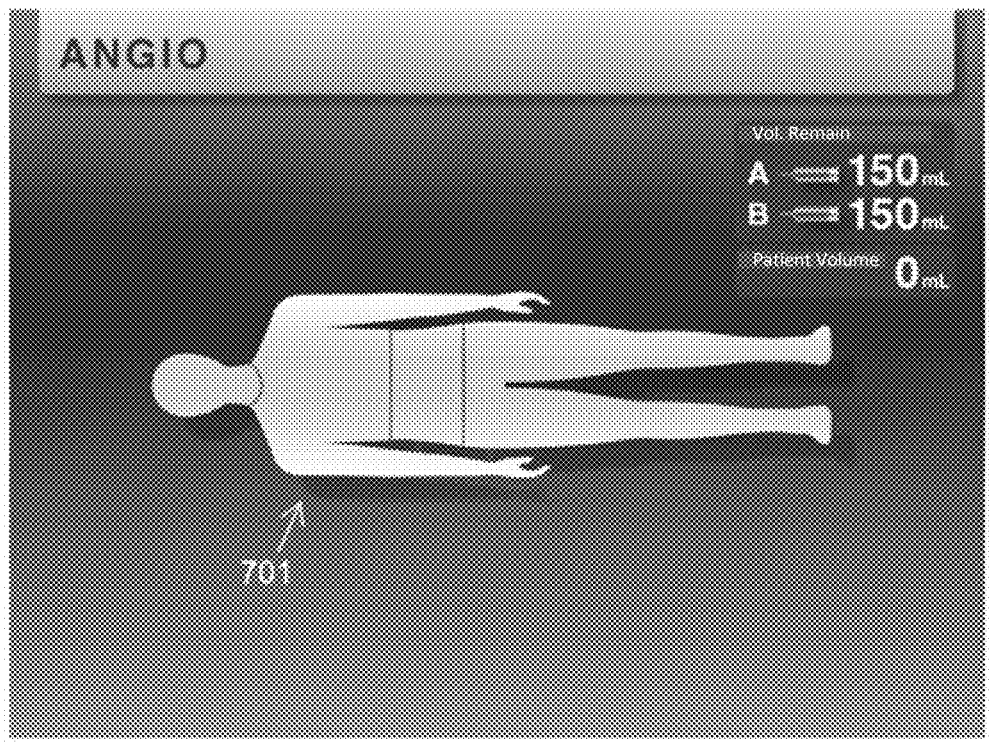
FIG. 7 is a graphical user interface (initial screen) for setting injection conditions.

The chemical liquid injector may display the following user interface images. Firstly, as in FIG. 7, a screen for selecting the imaging part is displayed. In this screen, an image 701 of a human body shape (also called as human body image 701) is displayed. The human body image 701 includes various regions, and in this example, a head region, a chest region, an abdominal region, and legs are displayed. Each region functions as an image button, and is selectable. In this screen, a remaining volume of each syringe set in the injection head 110 is also displayed.

Figure 8:
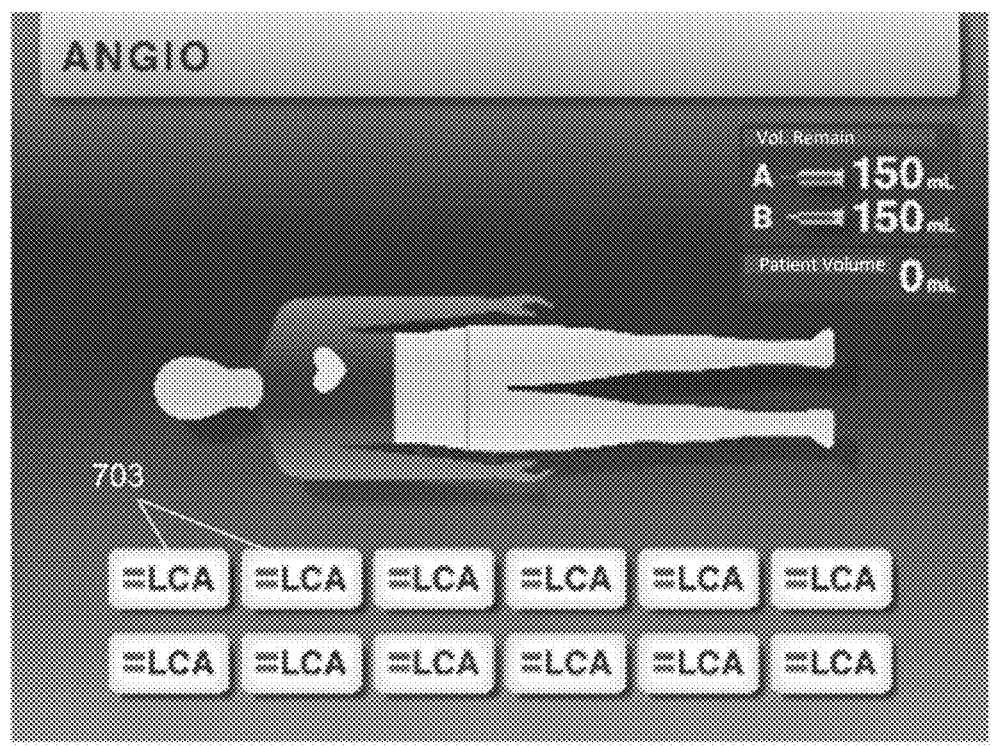
FIG. 8 is a graphical user interface (state in which, one of body segments is selected) for setting the injection conditions.

Next, when one part of the human body image 701 is selected, as shown in FIG. 8, one or a plurality of imaging parts 703 associated with that part is displayed. The imaging part 703 may be a plurality of different blood vessels for example. The imaging part 703 also functions as an image button, and is selectable.

Figure 9:
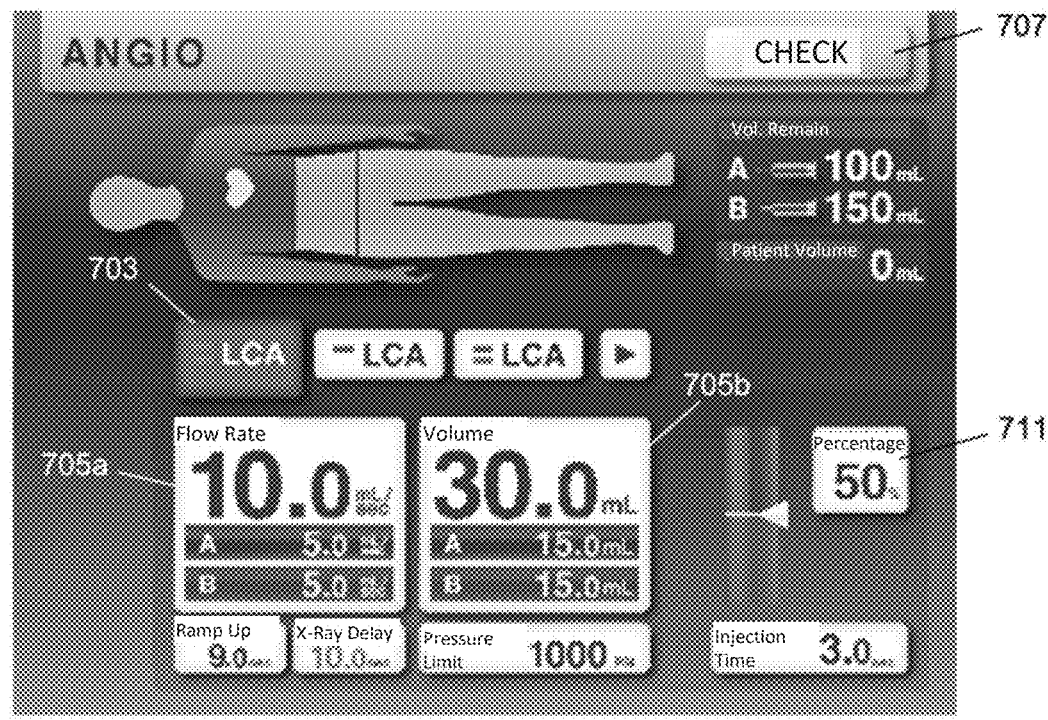
FIG. 9 is a graphical user interface (a state in which one of imaging parts (parts to be imaged) is selected) for setting the injection conditions.

Next, when one of the imaging parts 703 displayed is selected, chemical-liquid injection conditions associated with that imaging part 703 are displayed as shown in FIG. 9. Here, an injection-rate window 705a and an injection volume window 705b are displayed. In this example, information of the injection rate (10 mL/sec) and a display related to mixing conditions of a contrast medium and a physiological saline (injection rate of each chemical liquid) are included in the injection-rate window 705a. In this example, information of the injection volume (30 mL) and information of an injection volume of each chemical liquid are included in the injection volume window 705b. In a screen in FIG. 9, an image button 711 indicating information related to the mixing conditions of the contrast medium and the physiological saline is displayed. Specifically, information dilution percentage '50%' is displayed on the image button 711.

In an upper portion of the screen in FIG. 9, an image button 707 (also called as a check button 707) displaying 'check' is displayed. A checking state is a state in which, execution of both of a test shot (test injection) and a main injection are inhibited. Here, the 'test shot' refers to injecting a small dose (a volume smaller than the main injection. The injection rate may be slower than that of the main injection and/or the pressure condition may be lower than that for the main injection) of a contrast medium with a purpose of checking a front-end position of a catheter for example. The method may be such that the injection is continued only when the hand switch or the foot switch is being pressed, and when a state of not being pressed is assumed, the injection is stopped. In the state of FIG. 9, execution of the test shot is inhibited. By pressing the check button 707, the inhibited state is released, and execution of the test shot becomes possible.

Figure 10:
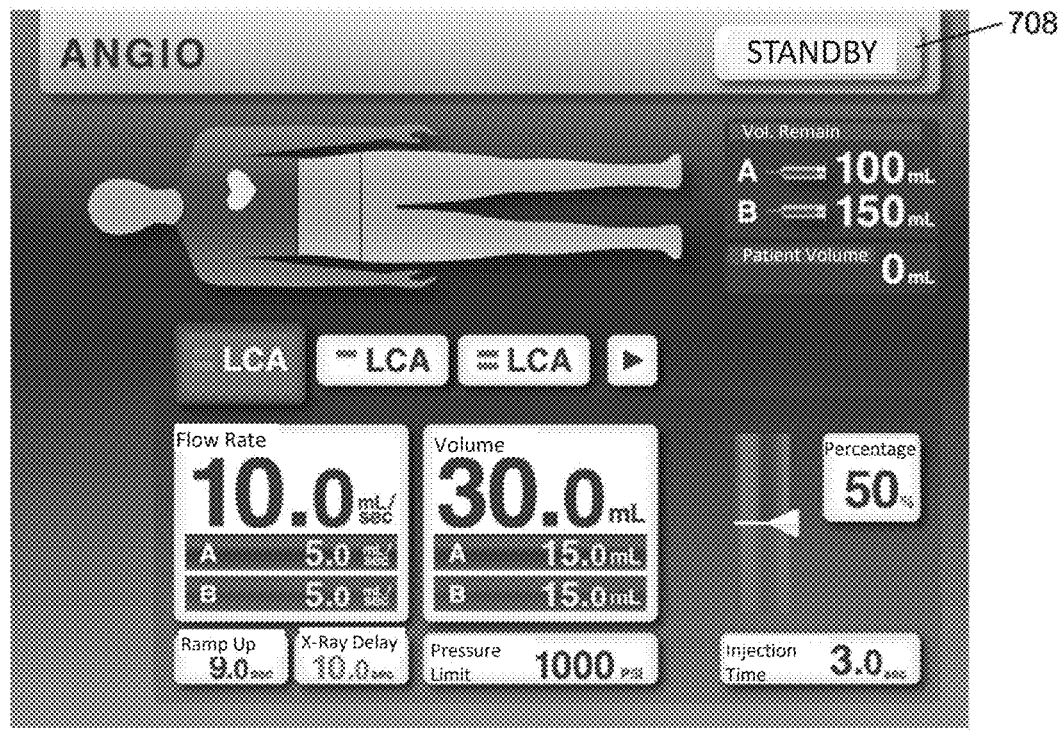
FIG. 10 is a graphical user interface (a standby state) for setting the injection conditions.

This state is a 'standby state' in FIG. 10. The standby state is a state in which, execution of the test shot is enabled but execution of the main injection is inhibited. In the standby state, when the catheter is moved to a predetermined target position inside a body of a patient, the operator thereafter presses a standby button 708.

Figure 11:
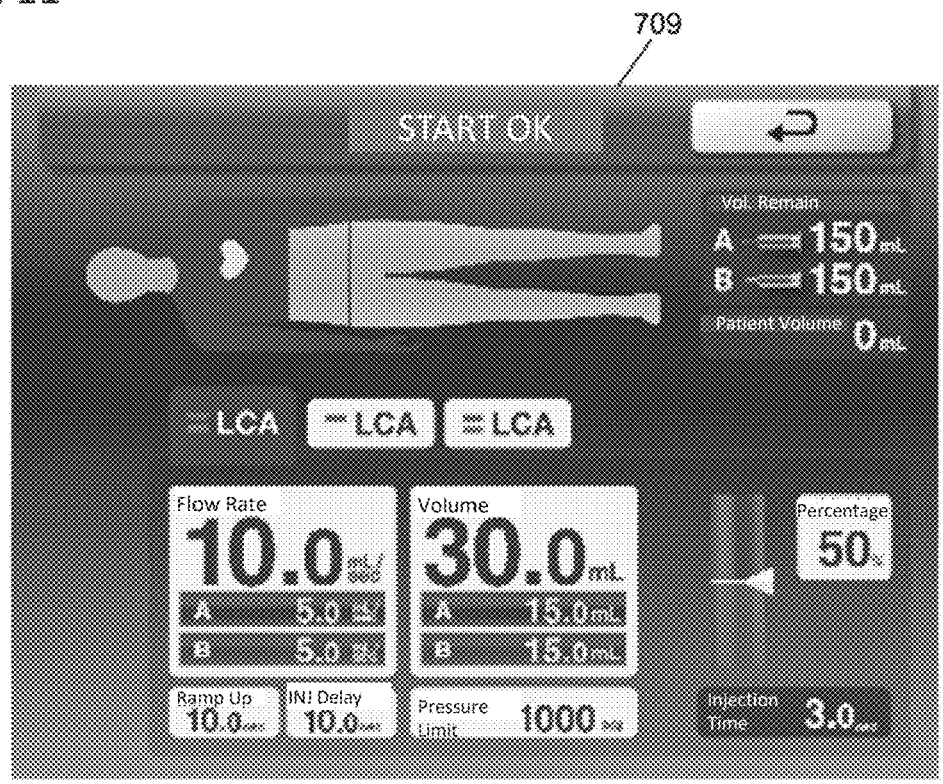
FIG. 11 is a graphical user interface (a start-OK state) for setting the injection conditions.

When the standby button 708 is pressed, there is a transition to a start-OK state in which an image button 709 having a display of start-OK as in FIG. 11 has appeared. The start-OK state is a state in which it is possible to start the chemical-liquid injection when there is a final input from the operator. For instance, by pressing the hand switch (or by pressing the foot switch), the chemical-liquid injection starts, the injection head functions in accordance with the injection conditions that have been set, and a desired chemical-liquid injection is carried out.

In the abovementioned description, although an example in which, when the part is selected on the screen of FIG. 8, there is a transition to the screen of FIG. 9 has been mentioned, the embodiment may be let to such that the screen of FIG. 9 is omitted, and after selecting the part, there is a transition directly to the screen of FIG. 10.

(b2: Numerical Keypad Window)

Figure 12:
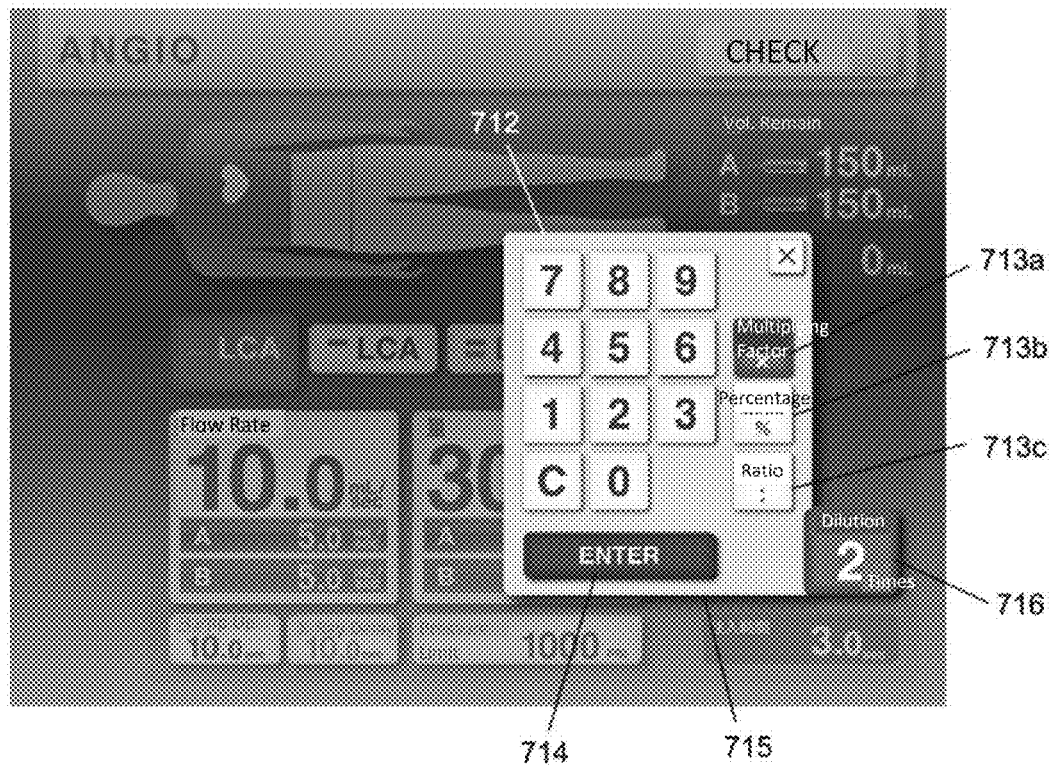
FIG. 12 is a graphical user interface (for changing dilution ratio) for setting the injection conditions.

In the present embodiment, a numerical keypad window 715 as shown in FIG. 12 may be displayed when the image button 711 for changing a numerical value related to a mixing condition (dilution condition) is pressed. In the numerical keypad window 715, a ten-key 712 and an enter key 714 are displayed, as well as a plurality of dilution setting buttons 713a to 713c is displayed. In this example, a multiplying factor method button 713a, a percentage method button 713b, and a ratio method button 713c are displayed as the dilution setting buttons.

These buttons 713a to 713c are for switching a method of inputting numerical values related to the mixing conditions. The multiplying factor method button 713a is for changing the dilution multiplying factor of the contrast medium such as 'twice', 'three times', and 'four times', and by pressing the multiplying factor method button 713a and selecting an arbitrary number by the ten-key, it is possible to input the multiplying factor.

The percentage method button 713b is for changing a mixing percentage of the contrast medium to a percentage such as '30%', '50%', and '70%'. The ratio method button 713c is for changing the mixing ratio of the contrast medium and the physiological saline to a ratio such as '1:1', '2:1', and '3:1'.

In such manner, since the present embodiment, the multiplying factor method button 713a, the percentage method button 713b and the ratio method button 713c are displayed to enable setting a number upon selecting any of the input methods, the operator is capable of inputting and correcting the number with the method used by the operator. In the abovementioned examples, although a configuration is such that three of the multiplying factor, the percentage and the ratio can be selected, only two of them may be displayed.

The abovementioned mode of changing numerical values of the mixing condition is terminated by confirming the changes by the enter key 714, or pressing an 'x' button displayed together with the numerical keypad window 715. The description made above is also applicable to a case of mixing a first chemical liquid and a second chemical liquid of different concentration, apart from the case of mixing a contrast medium and a physiological saline.

(b3: Injection-ON Screen)

Figure 13:
FIG. 13 is an example of a screen during chemical-liquid injection.

Next, an image to be displayed during chemical-liquid injection may be as an image in FIG. 13. In this image, a first syringe 717a, a second syringe 712b, and a mixing device 718 displayed at a location of merging of two chemical liquids are displayed. The mixing device 718 is a connector equipped with a function of mixing the two chemical liquids by generating a swirl flow at an interior thereof. Specifically, a device disclosed in Japanese Patent No. 5804543 can be used.

During the chemical-liquid injection, an animation display of a plurality of liquid droplets advancing toward the patient through a path 719a connecting the first syringe 717a and the mixing device 718 may be made, and an animation display of a plurality of liquid droplets advancing toward the patient through a path 719b connecting the second syringe 717b and the mixing device 718 may be made.

Moreover, an animation display of a pattern of oblique stripes indicating a swirl flow advancing toward the patient in the mixing device 718 may be made. In such manner, by making an arrangement such that the mixing device 718 is displayed on a screen during injecting, and, an animation display of mixing by the swirl flow in the mixing device 718 is made, the operator is able to make out visually and favorably that the injection using the mixing device is being executed.

Figure 14:
FIG. 14 is an example of a screen of a state in which the injection is stopped temporarily.

During the chemical-liquid injection, when the injection is stopped temporarily by a predetermined input (for instance, by a button being pressed) by the operator, a temporary-stop display 721 may be displayed as shown in FIG. 14 for example. By a predetermined input being made (by another button being pressed for instance) by the operator for restarting the injection, the temporary-stop display 721 goes out, and the screen in FIG. 13 appears once again and the injection restarts.

Figure 23:
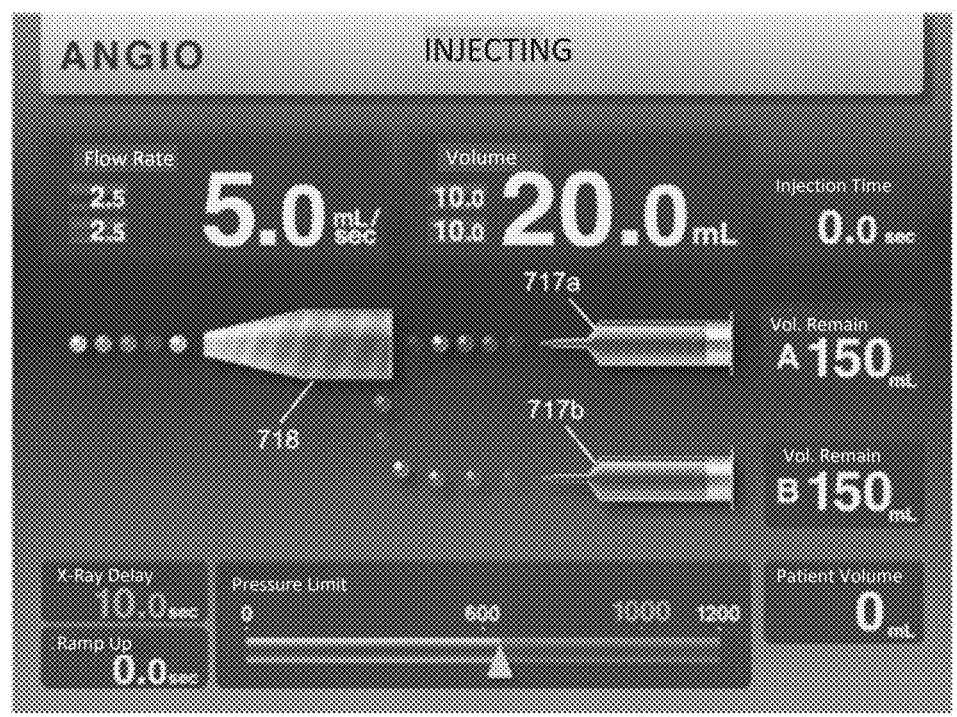
FIG. 23 is a diagram showing another example of a screen during chemical-liquid injection.

The image during injecting may be as in FIG. 23. In this image, the two syringes 717a and 717b are displayed in a smaller size as compared to that in FIG. 13. Whereas, the mixing device 718 is displayed in a larger size. The other components may be similar to those in FIG. 13, and in this example, a plurality of liquid droplets discharged from a front end of the mixing device 718 is displayed. An animation display of liquid droplets may be made similarly as in FIG. 13. Even in the image of FIG. 13, a plurality of liquid droplets may be discharged from the front end of the mixing device 718.

Figure 17:
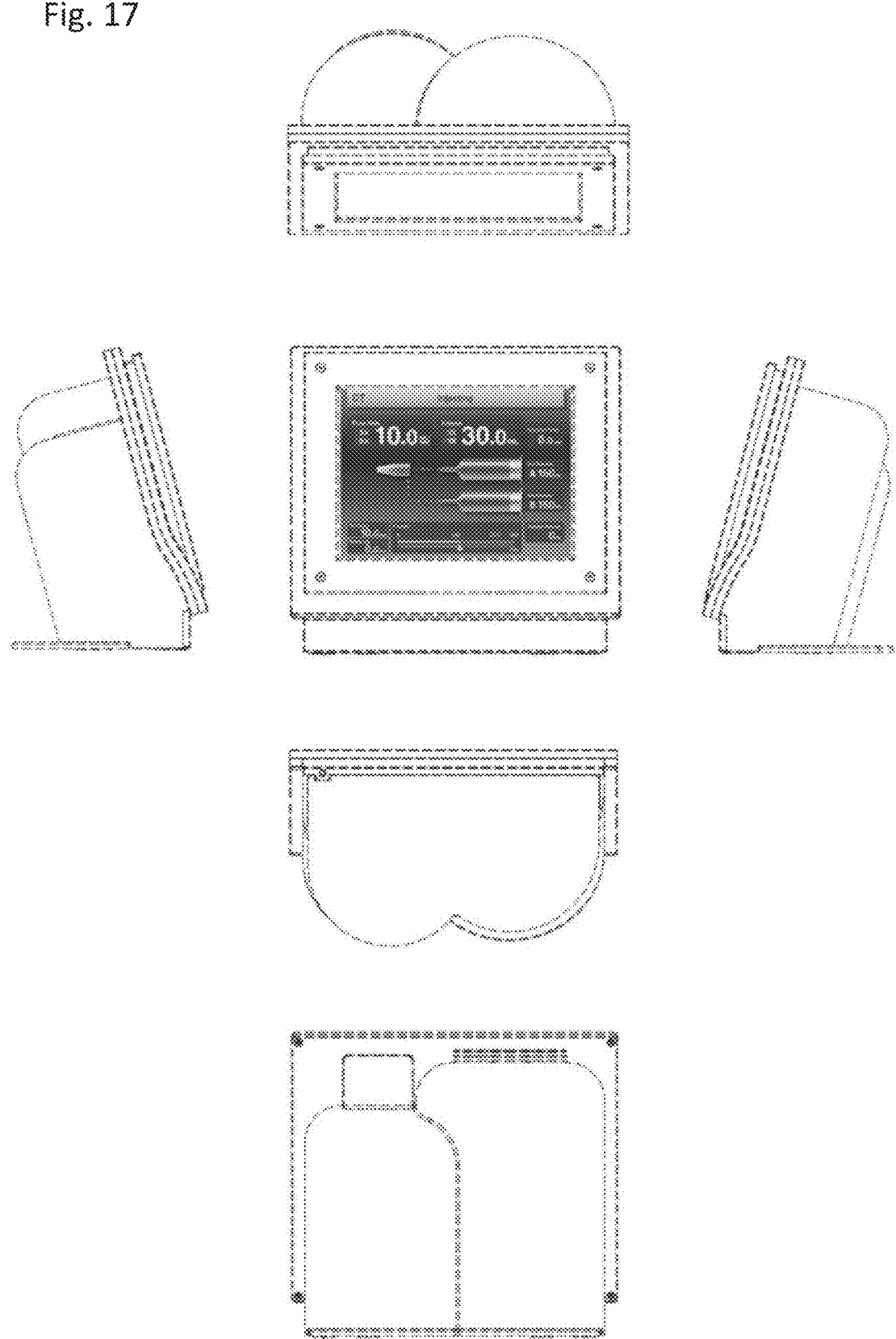
FIG. 17 is a six-face diagram of an operating device (console) of an injector for a chemical liquid injector having an image displayed on a display as a part of a design.

Note that, the present application, also discloses a partial design (see FIG. 17) with the images in FIG. 13 and FIG. 23 being a part of the design. Of the images in FIG. 13 and FIG. 23, only a part thereof (for instance, only the mixing device 718, only the display of the liquid droplets in the paths 719a and 719b, or a combination thereof and the syringes 717a and 717b) is a portion for which a design is to be obtained, and apart from this, a partial design depicted by broken lines is also disclosed. Alternatively, it may be one arbitrary combination or two or more than two arbitrary combinations of other components. The image of FIG. 23 may be replaced by an image displayed in the console in FIG. 17.

(b4: Screen Related to Part Selection Etc.)

Figure 15:
FIG. 15 is a graphical user interface (for changing imaging part) for setting the injection conditions.

Although the screen for setting the injection conditions was described previously while referring to FIG. 7 to FIG. 9, it may be as in FIG. 15. In this screen, the human body image 701 is displayed, and the chest region has been selected. Moreover, a plurality of imaging parts 703 (in this example, an LCA, an LVG, and an RCA and the like)

corresponding to the chest region is displayed. One of the plurality of imaging parts 703 has been selected.

The injection conditions associated with the imaging part 703 selected are displayed on the screen. Here, information such as the injection rate, the injection volume, and the injection time is displayed. Moreover, information of a delay time of injection, information of a rump-up time, and information of a pressure limit are also displayed.

The delay time is premised on a configuration that the operation of the chemical liquid injector and the operation of the imaging unit are in conjunction. In other words, in a case in which, firstly, a scan of the imaging unit starts, and the chemical-liquid injection starts after elapsing of a predetermined time, a time of delay with respect to a point of start of scan of the imaging unit is the delay time. In this example, the delay time is 10 sec for example. In the present embodiment, the display mode may be such that as the scan of the imaging unit starts, the display of the delay time goes on decreasing by a countdown method.

FIG. 15 illustrates a state in which one imaging part 703 (LVG) has already been selected. From this state, for selecting another imaging part 703, a method in which, the human-body image 701 (chest region), which is a broad category, is reselected once, and next, another imaging part 703 (for example LCA) which is a medium category is selected, may be possible. However, in the present embodiment, an arrangement is such that it is possible to switch directly to another imaging part 703 (for example from LVG to LCA) without reselecting the human-body part 701 which is a broad category. In other words, an arrangement is such that each of the plurality of imaging parts 703 in FIG. 15 can be selected, and by selecting one of these, directly, another imaging part is selected, and conditions associated with that are set. According to such selection method, since there being no need to reselect the human-body part 701 once, it is possible to carry out the operation in a simple and intuitive manner.

Figure 16:
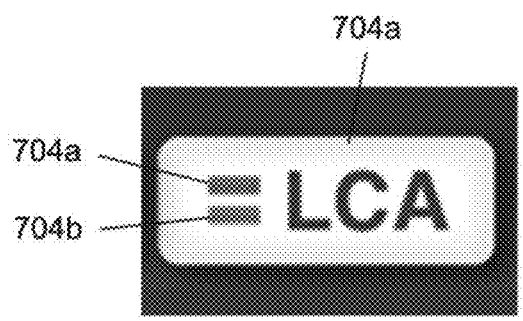
FIG. 16 is an example of an icon of the imaging part.

Regarding the imaging part 703, not only that simply a name (such as LCA, LVG, and RCA) of the target part is to be displayed, but also, indicators 704a and 704b indicating as to what sort of chemical liquid is to be injected may be displayed as shown in FIG. 16 for instance. The indicators 704a and 704b, respectively indicate that the first chemical liquid (contrast medium) and the second chemical liquid (physiological saline) are injected. In a case of injection of only the first chemical liquid, only the indicator 704a is displayed, in a case of injection of only the second chemical liquid, only the indicator 704b is displayed, and in a case of simultaneous injection, both the indicators 704a and 704b are displayed. The first chemical liquid (contrast medium) and the second chemical liquid (physiological saline) are displayed by different colors. According to such arrangement, it is possible to check visually the injection conditions that have been set for a certain imaging part, merely by looking at the button of the imaging part.

Figure 24:
FIG. 24 is a diagram showing an example of a display mode of the injection conditions.

An arrangement may be such that, as a screen after the part has been selected, there is a transition to a screen as in FIG. 24, apart from the screen in FIG. 9. In this example, the chest region from the body segmentation is selected, and 'LCA' from among the imaging parts, which is a subcategory thereof, is selected.

In an example in FIG. 24, a first phase is a mixed injection of two chemical liquids and a second phase is an injection only with one chemical liquid, and injection conditions of each phase are displayed in windows 1705a and 1705b respectively. Information of the injection rate and information of the injection volume is displayed in each window. Particularly, in the window 1705a of the first phase which is a mixed injection, information of the injection rate and the injection volume of the first chemical liquid, and information of the injection rate and the injection volume of the second chemical liquid are displayed. Although it is not limited, the window 1705a, which includes a lot of information in this manner, may be displayed in a size larger than a size of the window 1705b. The screen in FIG. 24, similarly as the screen in FIG. 9, is also a screen of the checking state.

(b5: Screen Display of Injection Result)

In angiography, a contrast medium is injected by moving a catheter to a predetermined location, and next, the contrast medium is injected with different injection conditions by moving the catheter to another target location, and subsequently, a similar process is carried out repeatedly. Therefore, as a screen display of the injection result, for instance, for example, for a certain patient, a plurality of results may be displayed in order such as a result of first injection (such as time, injection volume, injection rate, information about dilution, and part injected) and a result of second injection (such as, time, injection volume, injection rate, information about dilution, and part injected). Serial numbers (from 1 to 10 for example) may be assigned to the respective injection results, and the injection results may be displayed.

Note that, replacing a contrast medium syringe is also considered in angiography. For example, when the current syringe is removed from the injection head and another syringe in a protective case is set, a test for another patient is considered to have started, and injection results for the another patient are to be stored and displayed in order. A fact that the syringe has been set, as mentioned above, can be distinguished by an identification element provided to the protective case being identified by the injection head.

(Output of Injection Result)

Figure 25A:
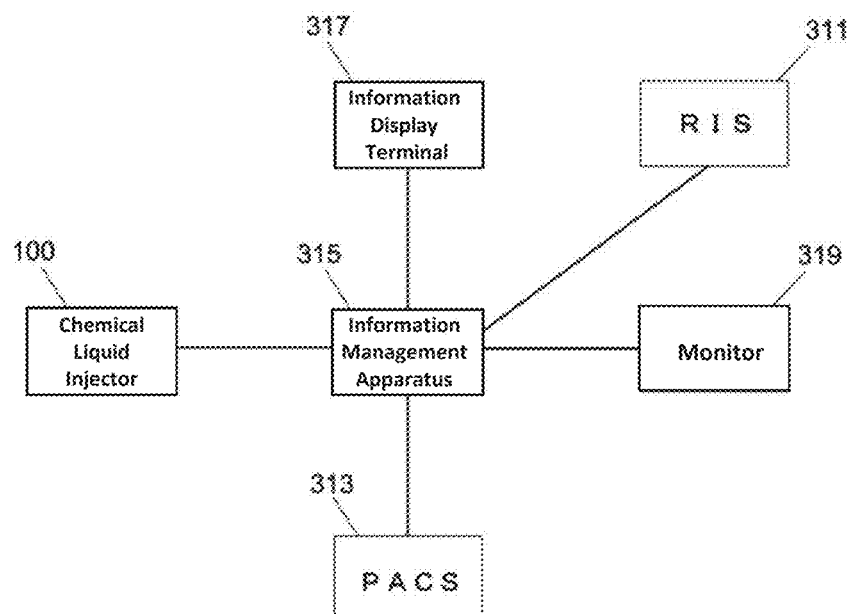
FIG. 25A is a diagram showing an example of a hospital system including the chemical liquid injector.

The chemical liquid injector and a system according to an aspect of the present invention may be configured such that, after the injection of a chemical liquid, information of the injection result thereof is output to outside. As shown in FIG. 25A, this hospital system includes the chemical liquid injector 100, an RIS 311, a PACS 313, an information management apparatus 315, an information display terminal 317, and a monitor in imaging room 319. Not all of the abovementioned components are indispensable, and one or a plurality of the components may have been omitted.

In such system, the chemical liquid injector 100 may be configured to output one or a plurality of the following information to the outside:
  information of a total volume of the chemical liquid to be injected,
  information of injection conditions (one or a plurality of conditions such as an injection pressure, an injection volume, an injection time, a body segmentation, an imaging part) that have been set
  various information related to the chemical-liquid injection (one or a plurality of conditions such as an injection pressure, an injection volume, an injection time, a body segmentation, an imaging part) that has been executed Although it is not limited in particular, an arrangement may be made such that this information is transmitted once from the chemical liquid injector 100 to the information management apparatus 350, and the information management apparatus 315 carries out communication with each instrument, and transmits the information.

The information display terminal may be, for example, may be a portable tablet terminal, and at least one of the abovementioned information may be displayed on this tablet terminal.

It is preferable that an arrangement is made such that, by using information such as the information of total volume of the chemical liquid to be injected, a predetermined accounting process is carried out in the system. The information management apparatus 315 may be configured to read patient information from the RIS 311. In this case it is preferable that the information management apparatus 315 is capable of transmitting information of the injection result and also the patient information to each instrument (at least one of information display terminal 317, imaging room monitor 319, and PACS 313. Moreover, in a case in which, information related to a renal function of that patient (such as a value of an estimated glomerular filtration rate (eGFR)) is included as the patient information, that information may be transmitted to an arbitrary instrument in the system, and a processing of, the information being used for a judgment of suitability of the test, and being displayed appropriately, may be carried out.

Figure 25B:
FIG. 25B is a diagram showing an example of an injection result display.

Note that, as the injection result, as in FIG. 25B for example, a plurality of injection result displays 1761 may be displayed for each of a series of tests. The injection result display 1761 includes for example, a test number, date, a time of start of injection, total volume injected of the chemical liquid in that test, and information of a part which was tested. One or a plurality of this information may be omitted, or other information not shown in the diagram may be included.

In this example, 10 injection result displays 1761 from '1' to '10' are displayed on one screen. In a series of tests, as to which interval of timings (from which timing up to which timing) is to be put together in one injection result display 1761 may be determined appropriately freely, and in the present embodiment, it may be as follows for example. In other words, a series of tests for a certain patient is over and the syringe is removed from the clamper 145 of the injection head 110 (see FIG. 2). Thereafter, a subsequent new syringe is set in the clamper 145. When it has been detected that the clamper 145 was opened, or closed, or both opened and closed, the injection result display 1761 of the subsequent test may be prepared automatically (for example, if the previous test was '1', the injection result display 1761 of '2' is prepared automatically). Such processing may be executed not only with the opening and closing of the clamper 145 as a trigger, but also the attaching and detaching of the syringe or the protective case as a trigger.

Note that, in the screen of FIG. 25B, a mode display 1762 indicating a mode of the chemical-liquid injection that was carried out is also included. As the mode display 1762, a mode such as 'angiography', 'infusion', and 'CT' may be displayed. In the apparatus of the present embodiment, it is possible to execute a plurality of modes such as an 'angiography mode', an 'infusion mode', and a 'CT mode' (details will be described later). Here, for instance, let us assume that the first test was the angiography mode, the subsequent test was the infusion mode, and the following test was the CT mode. A method of displaying the injection result may be by displaying these three modes together on one screen. In the present embodiment, the method of displaying is as follows. In other words, for each mode, the results of injection executed are grouped and then displayed. That is, in an example in FIG. 25B, since the mode display 1762 of angiography has been selected, all the results '1' to '10' displayed here are results for the angiography mode. The three mode displays 1762 can be selected as image buttons, and for instance, when infusion is selected, a series of injection results that have been grouped as the infusion mode is displayed and when CT is selected, a series of injection results that have been grouped as the CT mode are displayed. According to such display, it is possible to verify for each mode, the result of chemical-liquid injection that has been executed, and is useful.

Figure 25C:
FIG. 25C is a diagram showing an example of a detail display of the injection result.

By selecting one of the plurality of injection result displays 1761 in FIG. 25B, a detail result included therein may be displayed as in FIG. 25C for example. In a screen of FIG. 25C, details of the injection result of number '9' are displayed in a window 1763 as an example. Although it is not limited, content of the detail result, for instance, may be one or a plurality of information related to the following items: a time at which the chemical-liquid injection was carried out, the maximum rate, an injection volume, the number of injection phases, whether it was an injection of a single chemical liquid or a simultaneous injection (dilution injection) of a plurality of chemical liquids, an injection time, an injection pressure, a targeted part, a mixing ratio, a multiplying factor for mixing, a mixing percentage, a delay time, and a ramp-up time. This information may be grouped for each test and procedure executed for example, and may be displayed upon assigning numbers '1' and '2' for example. Moreover, information of the total volume injected in a series of injections may be displayed as the detail information. As a specific example of display of the detail result, display by using an indicator as explained by referring to FIG. 16 may be carried out. For example, assuming that an injection including a first phase (dilution injection) and a second phase (injection of only a single chemical liquid) was executed, in order that this is revealed visually, two indicators are displayed as indicators corresponding to the first phase, and one indicator is displayed as an indicator corresponding to the second phase (see a display content of a result numbered '3' in FIG. 25C. The indicator of the second phase is displayed on the right of the indicators of the second phase.). Such display using indicators is preferable as it enables to know accurately the injection content of each phase by looking at the number and a color of indicators. Moreover, as compared to a case of displaying textual information, since it is possible to give an adequate amount of information even with a relatively small size, the display using the indicator is particularly favorable for the display of injection result in a form as in FIG. 25C.

(b6: Other Screen Displays)

Figure 19:
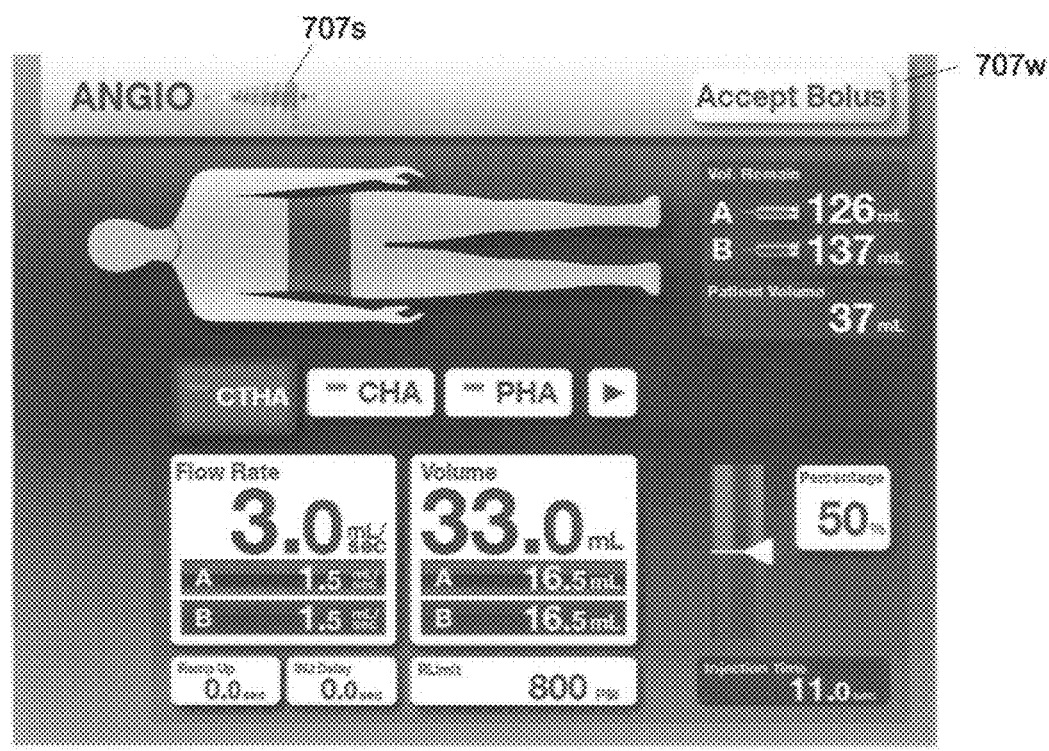
FIG. 19 is an example of a screen including an image indicating that it is a mixture for which a mixing device is used.

As a display showing that it is a mixture using a mixing device, it may be a mixing device image 707s displayed in a predetermined window 707w of a screen as in FIG. 19. The window 707w, in this example, is a bar-shaped window near an upper end of the screen. By a mixing device image 706s being displayed in such manner, the operator can verify intuitively that it is a mixture using a mixing device.

Figure 20:
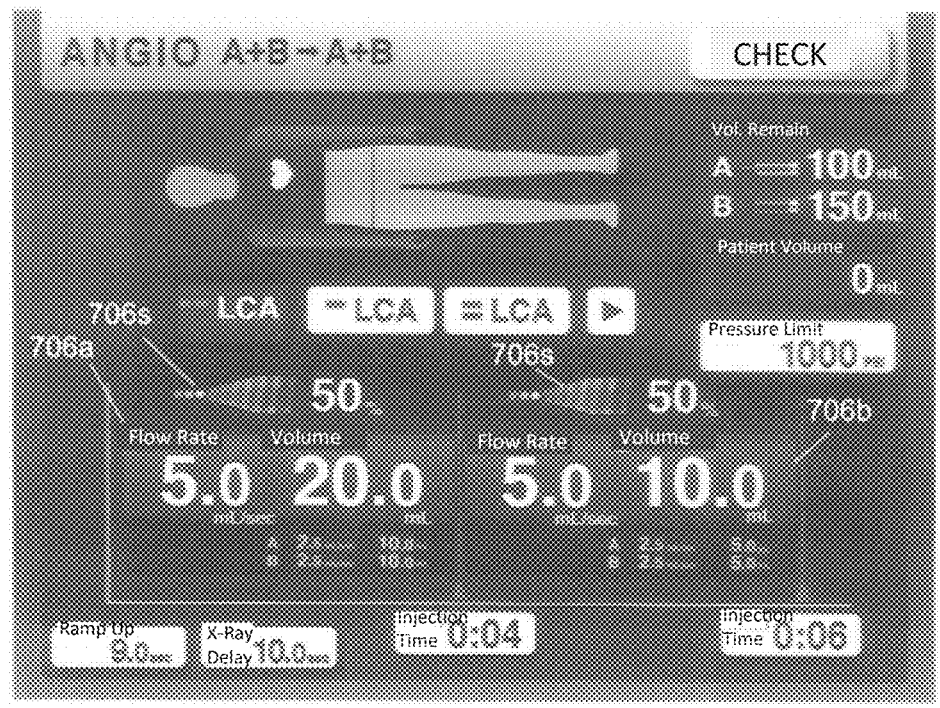
FIG. 20 is another example of a screen including an image indicating that it is a mixture for which a mixing device is used.

Moreover, the display may be in the form as in FIG. 20. In this example, injection conditions including two phases are set, and injection conditions (such as, an injection rate and an injection volume) of the two phases are displayed in a first phase display portion 706a and a second phase display portion 706b respectively. Moreover, the mixing device image 706s is displayed in the first phase display portion 706a and the second phase display portion 706b. This indicates that a mixed injection is carried out in each phase.

Figure 22:
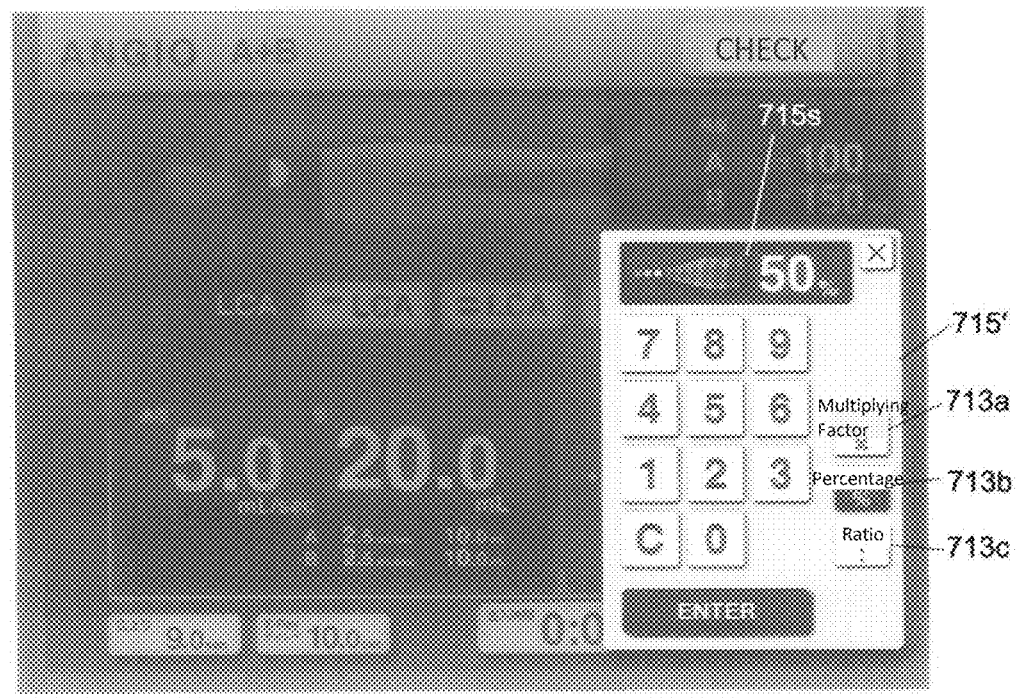
FIG. 22 is an example of a graphical user interface for setting the injection conditions.

The mixing device image 706s may function as an image button. When the mixing device image 706s is pressed, a predetermined injection condition changing screen (for example, FIG. 22) may be displayed. In an example in FIG.

22, a numerical keypad window 715', which is by and large similar to the numerical keypad window 715 in FIG. 12, is displayed, and dilution setting buttons 713a to 713c are displayed in this window. Moreover, a mixing device image 715s and/or a current dilution percentage (here, 50%) may be displayed in the same window.

Figure 21:
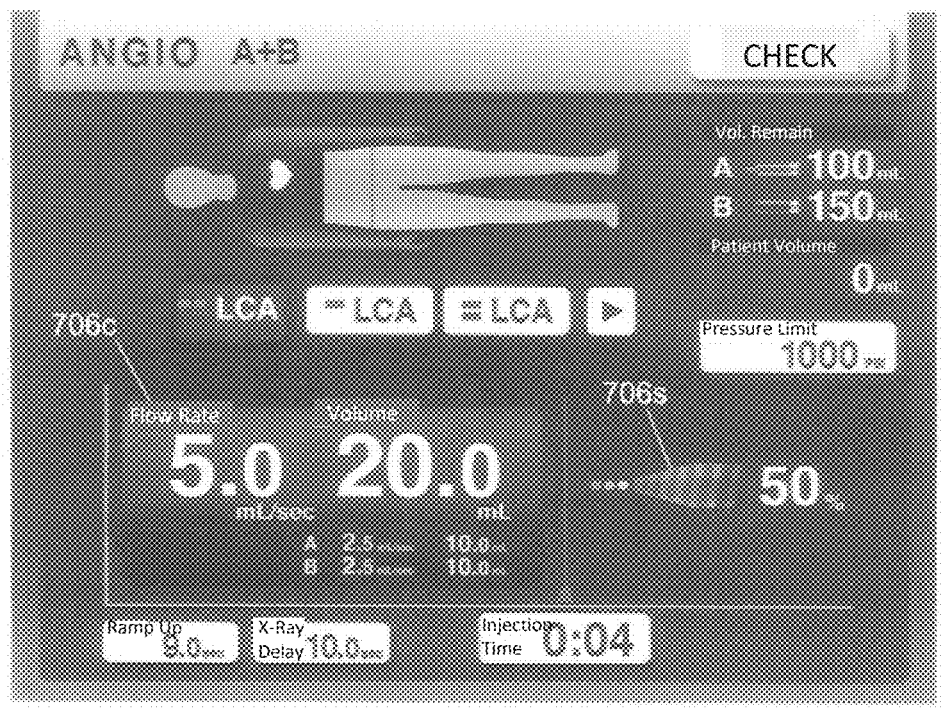
FIG. 21 is still another example of a screen including an image indicating that it is a mixture for which a mixing device is used.

As the display form in FIG. 21, only the first phase display portion 706a may be displayed, and the mixing device image 706s may be displayed near (by the side, in this example) thereof. The image as well, similarly as mentioned above, may function as an image button.

Specific embodiments of the present invention have been described heretofore while referring to the diagram; however, it is possible to make appropriate modifications in the present invention without departing from the scope of the present invention.

(1) For instance, in the embodiment described above, displaying the graphical user interface on the display of the console was explained; however, apart from this, a function as mentioned above may have been installed in a work station and a tablet provided as a desk-top computer.

A series of graphical user interface display forms described above can be expressed as an invention related to a method of display, and moreover, can be expressed as an invention of a computer program for making a computer execute that method.

(2) For instance, the injection head may have a tilt sensor which detects an inclination of the injection head. Generally, in this type of injection head, the suction of a chemical liquid into the syringe is carried out in a posture of a front-end side thereof (that is, a syringe side) becoming upward. Whereas, the chemical-liquid injection is executed in a posture of the front-end side of the injection head directed relatively downward (a posture in which the tip side is directed somewhat downward). By using a detection result of the tilt sensor, it is possible to prevent the chemical-liquid suction or the chemical-liquid injection in an undesirable posture. Moreover, the control may be carried out such that, on the basis of the detection result of the tilt sensor, it is identified whether the injection head is directed upward or downward, and a direction of characters etc. displaying the display unit 146 is flipped vertically. According to such arrangement, the operator can realize the display content favorably.

Figure 18:
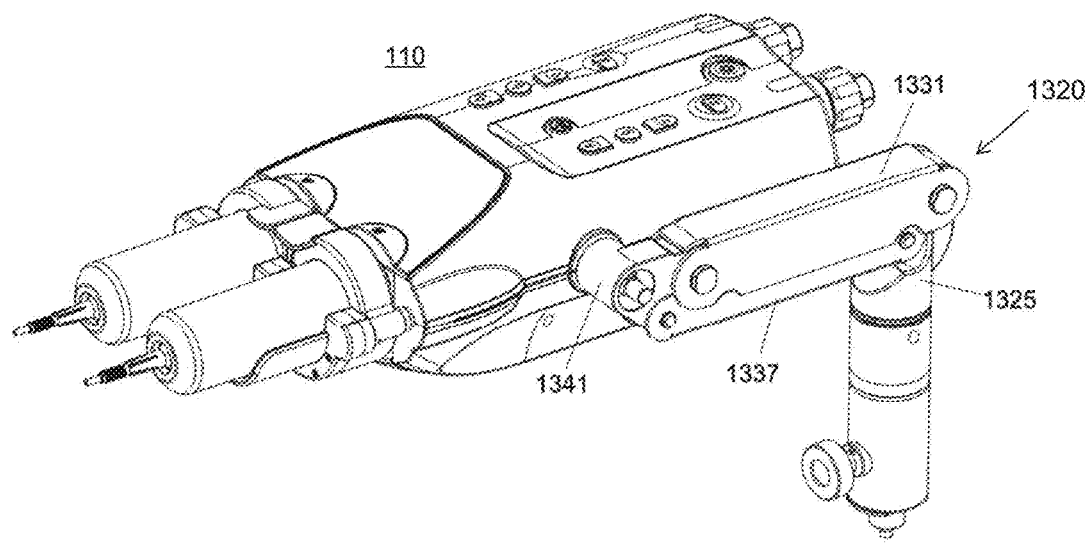
FIG. 18 is a perspective view showing an example of a holding mechanism of the injection head.

(3) A mechanism which holds the injection head 110 may be as shown in FIG. 18. A holding mechanism 1320 includes a base portion 1325, a first arm member 1331 which is pivotably attached to the base portion 1325, a second arm member 1337 which is pivotably attached to the base portion 1325, and a holding member 1341 having each of end portions on a front-end side of the first arm member 1331 and the second arm member 1337 pivotably attached thereto, and the injection head 110 fixed thereto. A parallel link is formed by the base portion 1325, the first arm member 1331, the second arm member 1337, and the holding member 1341.

The base portion 1325 is to be fixed to a predetermined installing position of a movable supporting column or a bed of the imaging apparatus via or not via another member. The holding mechanism in FIG. 18 being provided as a parallel link mechanism, it can be pivoted in a frontward and rearward direction in the same posture of the injection head 110.

Figure 26:
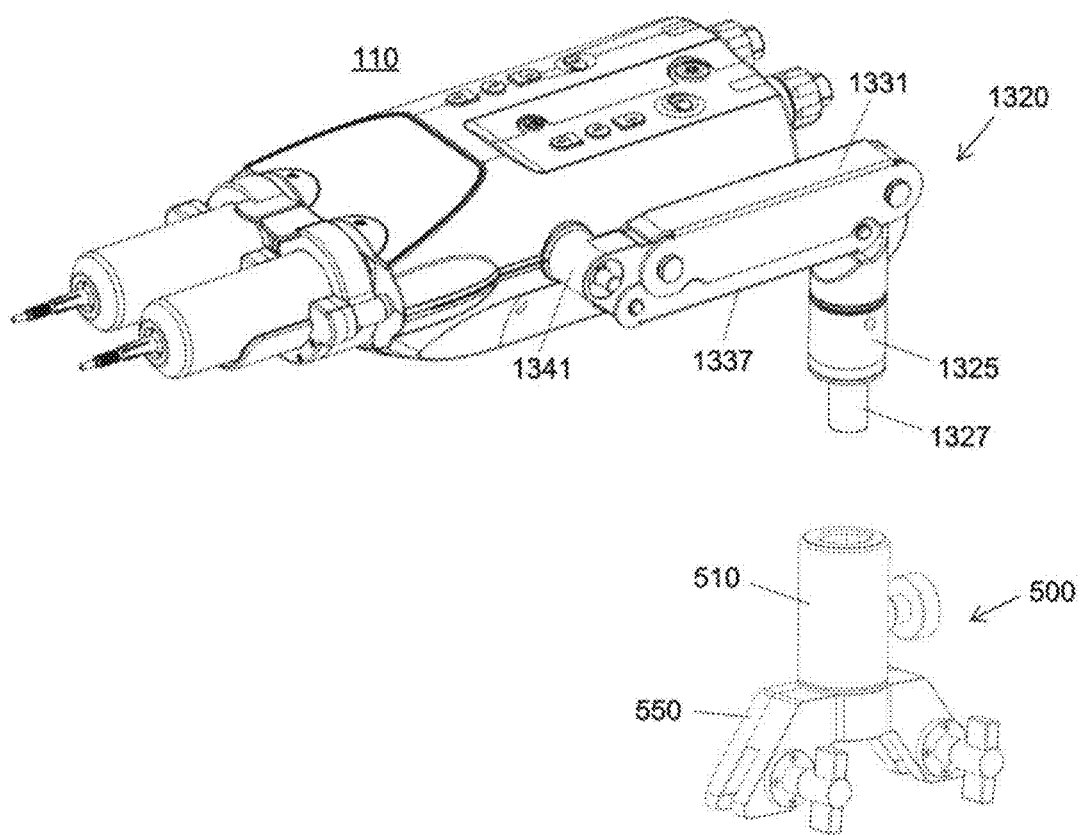
FIG. 26 is a perspective view showing an example of a mechanism for holding the injection head.

For installing the injection head holding mechanism 1320 in FIG. 18 at a predetermined location in a medical facility or on a predetermined medical instrument, it is possible to use an installation mechanism as in FIG. 26. An installation mechanism 500 is for fixing the injection head to a guide rail (details described below) of the imaging apparatus.

The installation mechanism 500, when broadly divided, includes a holding assembly 510 for holding a part of the injection head holding mechanism 1320 and a base assembly 550 supporting the holding assembly 510. Note that, the holding assembly 510 and the base assembly 550 may be separate components or may be formed integrally.

Figure 27:
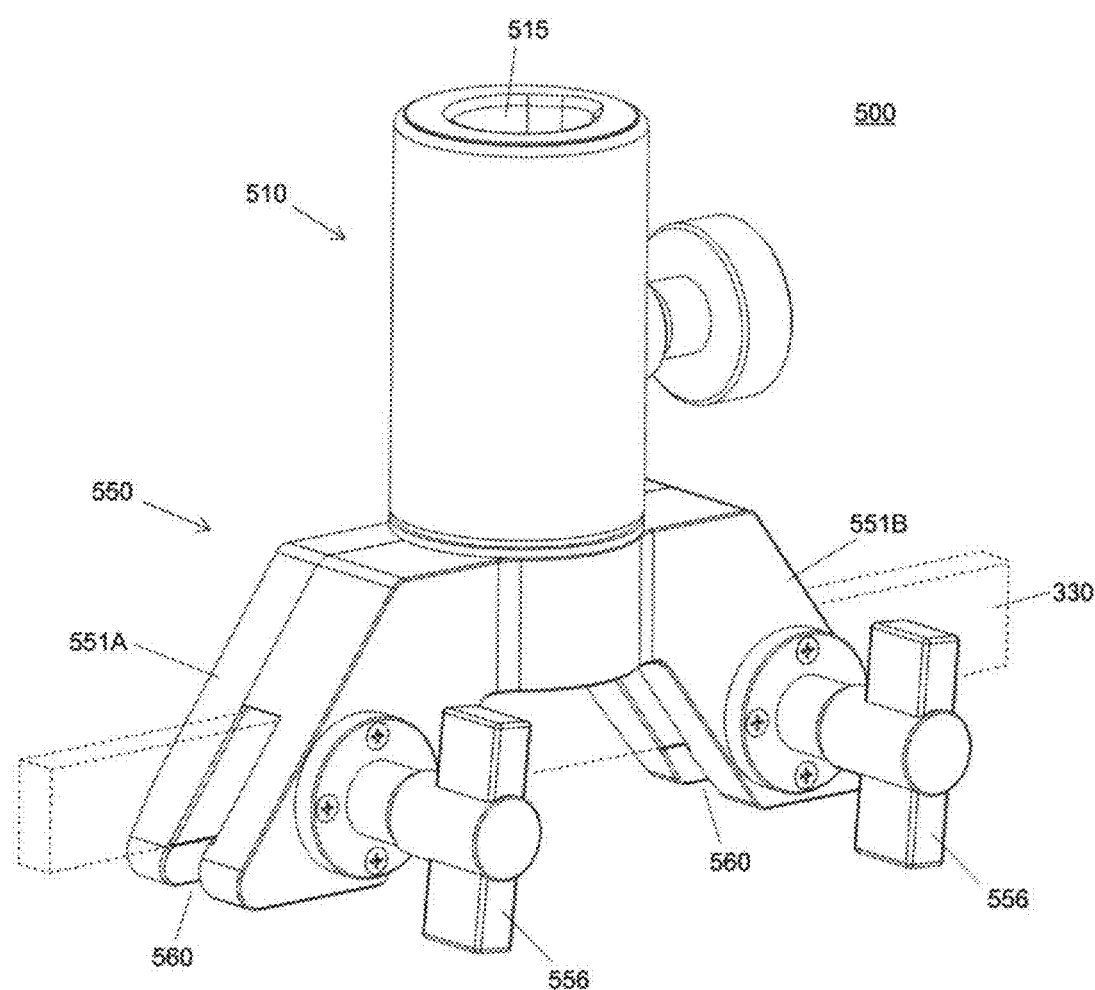

The holding assembly 510, as shown in FIG. 27, is a member having a receiving hole 515 through which, a round shaft 1327 provided to the injection head holding mechanism 1320 is inserted. The receiving hole 515, in this example, is a round hole formed to be extended vertically. A detail structure of the receiving hole 515 and a structure for fixing the round shaft 1327 will be described later by referring to another diagram.

The base assembly 550 is a member which is removably fixed to a rail 330. The guide rail 330 is provided to a side portion of the bed of the imaging apparatus, and various medical instruments are installed according to the requirement. The guide rail 330, in general, is a metallic long member having a rectangular cross section.

The holding assembly 510 is fixed on an upper-surface portion of the base assembly 550. The base assembly 550, in this example, is to be installed on the guide rail 303 by mounting from above. The base assembly 550, as shown in FIG. 27, has two extending portions 551A and 551B extended downward. The extending portions 551A and 551B (also referred to as extending portion 551 without distinguishing) are provided with a receiving groove 560 formed vertically upward from a lower-surface side, and the guide rail 330 is to enter in this groove.

Figure 28:
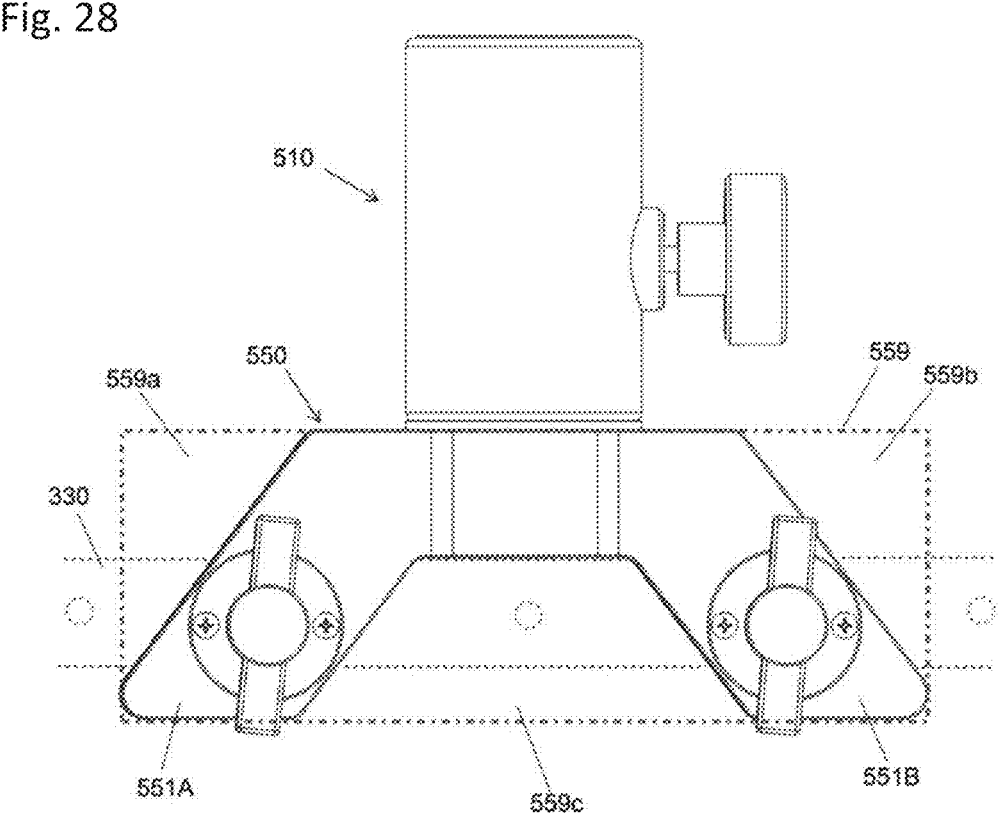
FIG. 28 is a diagram of the installation mechanism of FIG. 27 viewed from a front side.

An overall shape of the base assembly 550 is not limited in particular, and in the present embodiment, is a substantially upside-down V-shape (made by a horizontal portion and two portions extending to be inclined downward from both ends of the horizontal portion) as shown in FIG. 28 (diagram when viewed from a direction perpendicular to a side surface of the guide rail 330). The base assembly 550 may include a block-shaped member having a rectangular parallelepiped shape as shown by a reference numeral 559 in FIG. 28, and in the present embodiment, has an overall shape in which shoulder portions 559a and 559b on left and right, and a central bottom portion 559c of such block-shaped member 559 are cut out. Accordingly, the structure is compact and light, while maintaining a stability of holding.

Figure 29:
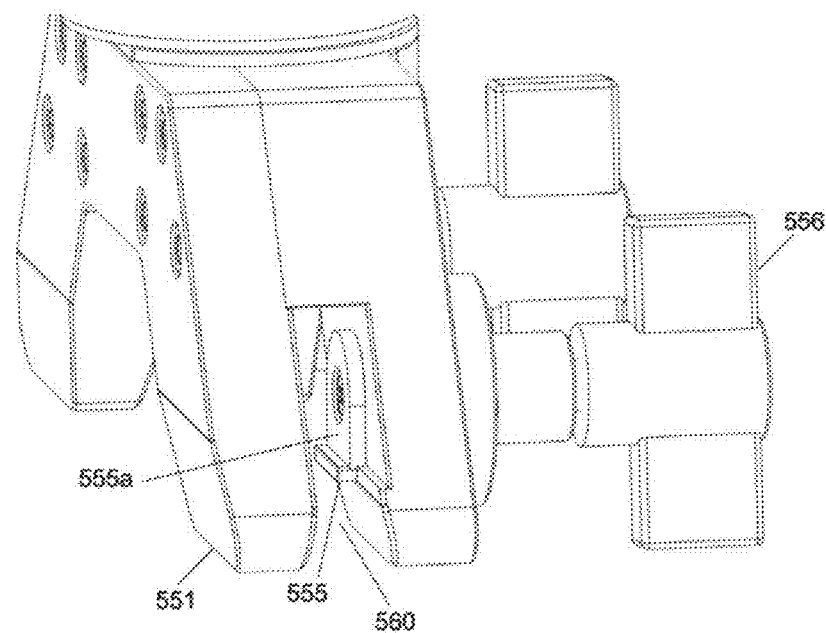
FIG. 29 is a perspective view showing in detail the installation mechanism of FIG. 27.
Figure 30:
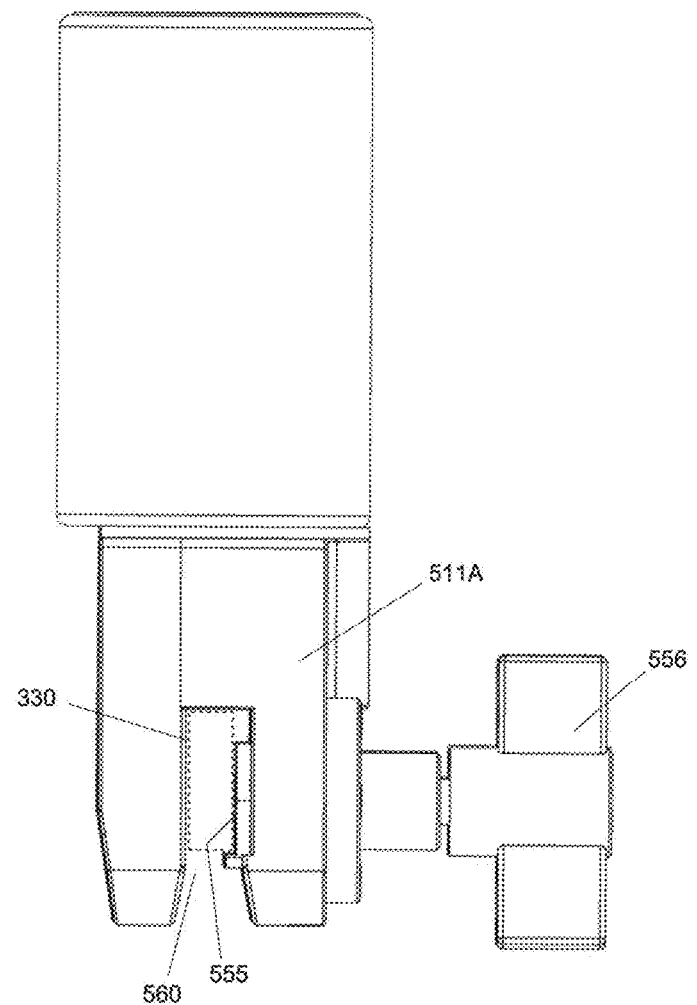
FIG. 30 is a diagram of the installation mechanism of FIG. 27 viewed from a side-surface side.

As shown in FIG. 29 and FIG. 30, the extending portion 551 is provided with a tightening handle 556; and by turning the tightening handle 556, an abutting member 555 moves into the receiving groove 560. The abutting member 555, in this example, has a pushing surface 555a which is flat, and this pushing surface is to abut with the guiderail side surface.

Figure 31:
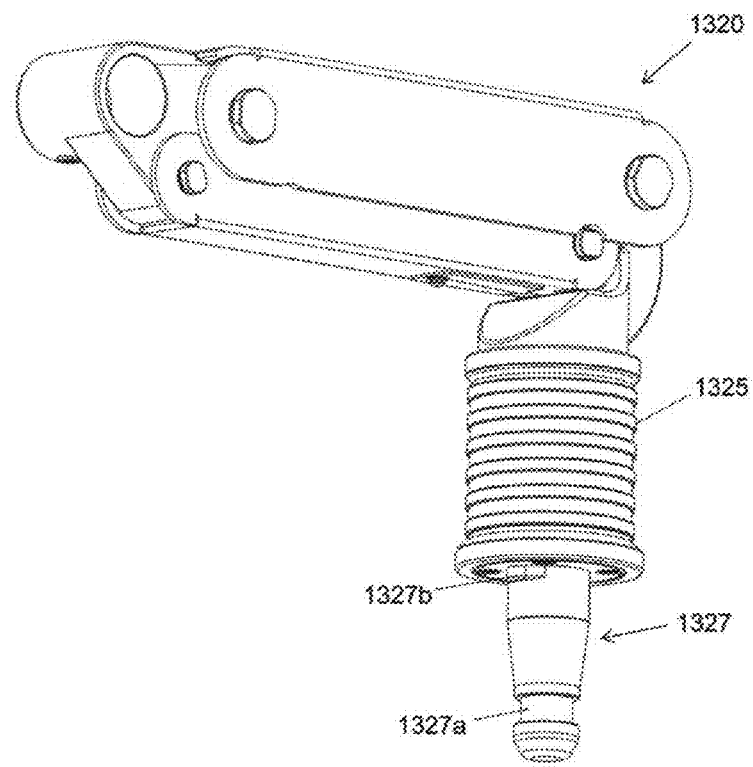
FIG. 31 is a perspective view showing an example of a holding mechanism of the injection head.
Figure 32:
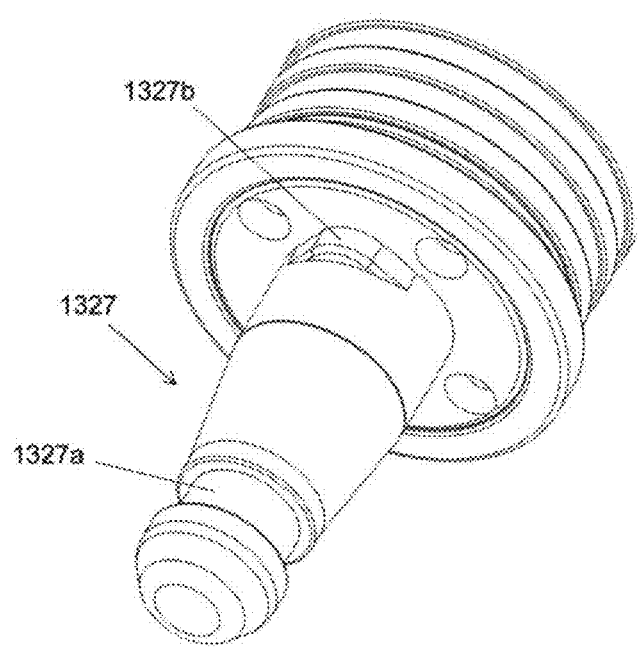
FIG. 32 is a perspective view showing in detail the holding mechanism in FIG. 31.

A mechanism of holding by the holding assembly 510 will be explained by referring to FIG. 31 to FIG. 34. As shown in FIG. 31 and FIG. 32, the round shaft 1327 of the holding mechanism 1320 protrudes downward from the base portion 1325, and a recess 1327a is formed in a portion of the round shaft 1327. The recess 1327a is a portion where a diameter of the round shaft 1327 is made small partially, and here, an abutting member 527 of the holding assembly 510 that will be described later, has to fit in. A key portion 1327b projected from the shaft toward an outer side of a radial direction is formed near a base-end portion of the round shaft 1327. Although it is not limited, the key portion 1327b may have a shape of a mound formed by two oblique sides on left and right and an apex portion connecting the two oblique sides by a gentle curve.

Figure 33:
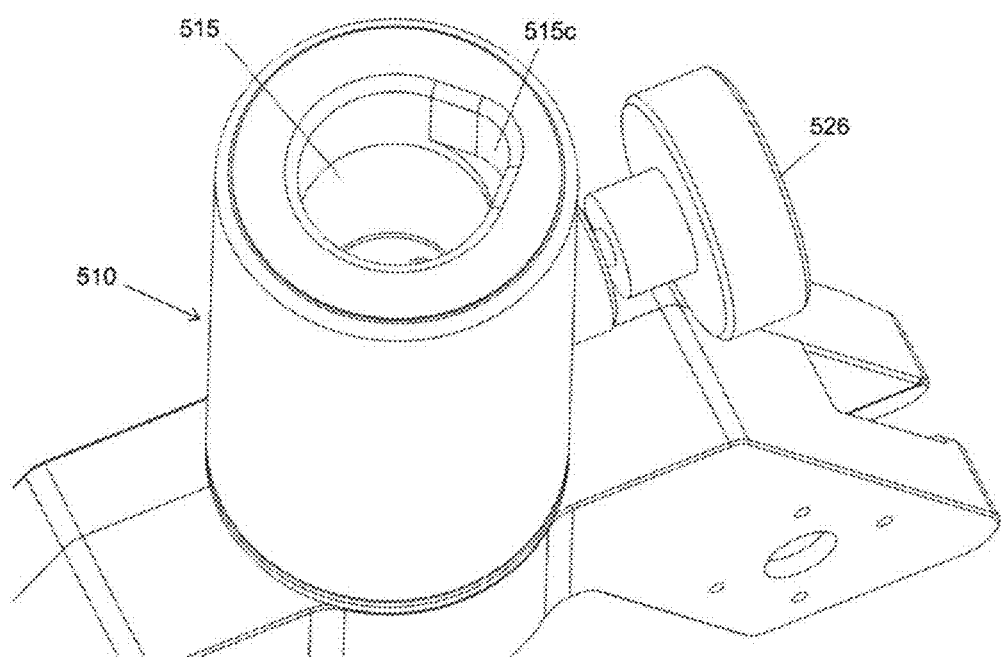
FIG. 33 is a perspective view showing in detail the holding mechanism (holding assembly) in FIG. 31.
Figure 34:
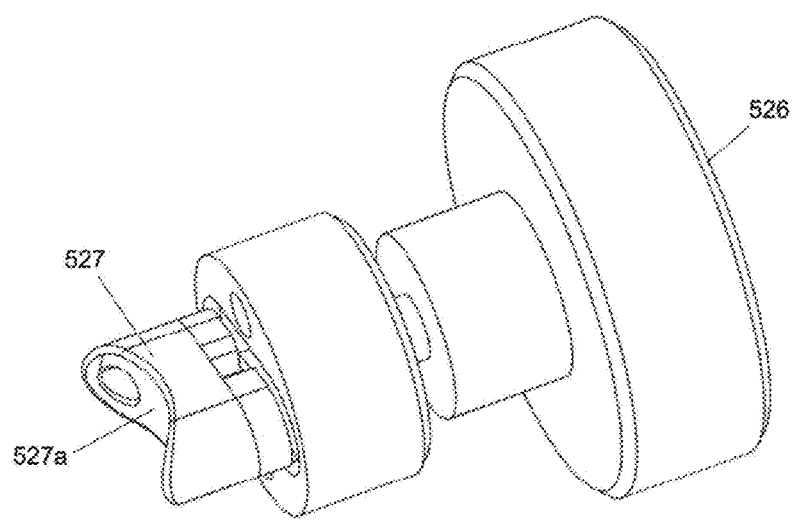
FIG. 34 is a perspective view showing in detail the holding mechanism (handle) in FIG. 31.
Figure 35:
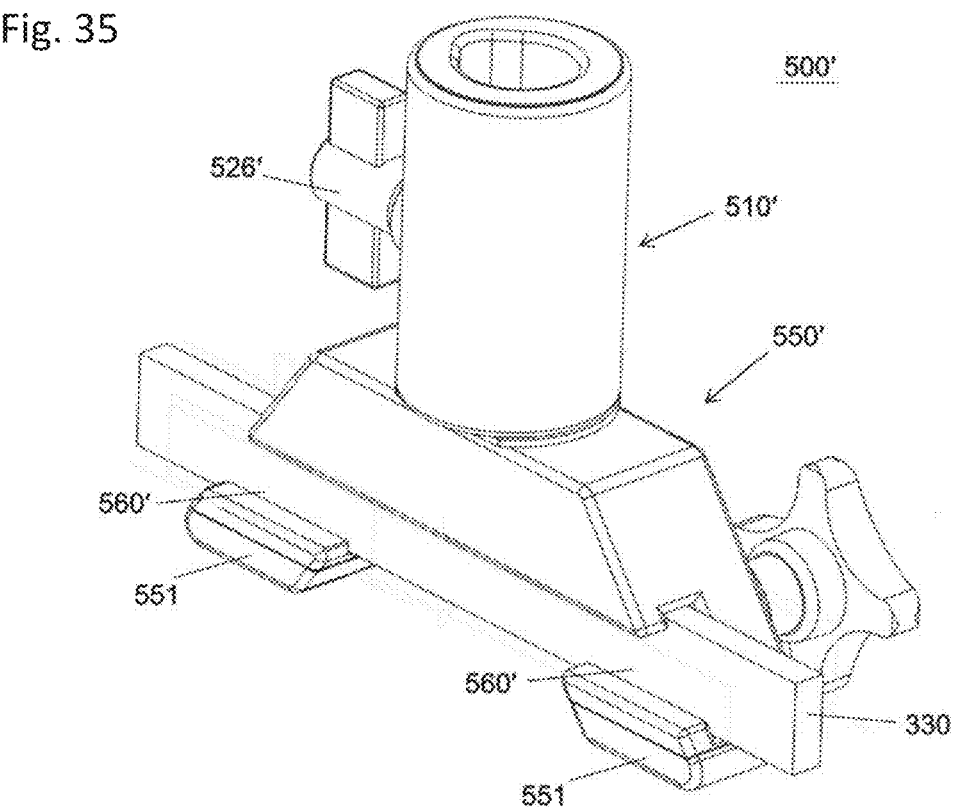
FIG. 35 is a perspective view showing another example of the installation mechanism of the injection head.
Figure 36:
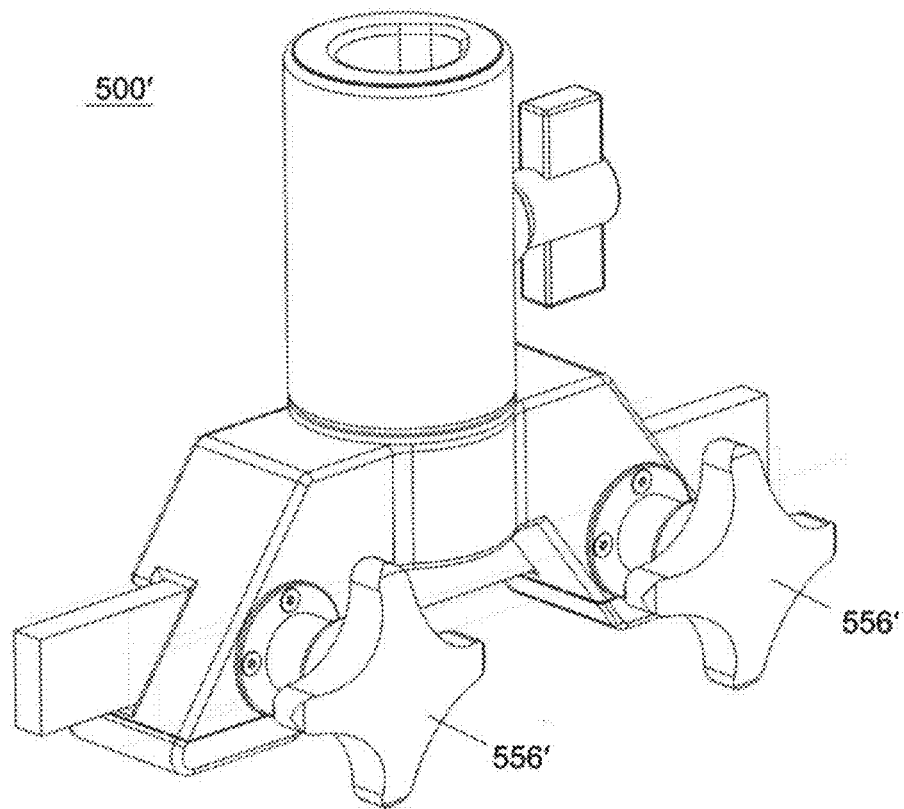
FIG. 36 is a perspective view showing another example of the installation mechanism of the injection head.

The round shaft 1327 formed in such manner is inserted into the receiving hole 515 of the holding assembly 510. As shown in FIG. 33, a recess 515c (having shape complementary to the key portion 1327b) is formed, and by installing the round shaft 1327 such that the key portion 1327b of the round shaft 1327 is fitted into the recess 515c, rotation of the round shaft 1327 is regulated.

By turning a handle 526 provided to the holding assembly 510, an engaging member 527 advances into the receiving hole 515. The engaging member 527 has at a front end, a curved surface 527a which is to be along an outer periphery of the recess 1327a of the round shaft 1327. When the engaging member 527 is moved in up to a predetermined position, a front end portion of the engaging member 527 is in a state of being entered into the recess 1327a, and accordingly, the round shaft 1327 is prevented from coming off the receiving hole 515.

In the abovementioned holding structure, both a movement in a direction of rotation of the round shaft 1327 and a movement in an axial direction of the round shaft 1327 are regulated. Consequently, the round shaft 1327 is prevented from coming off due to an unexpected cause, and the holding mechanism 1320 (and furthermore the injection head 110 held by the holding mechanism 1320) is prevented from falling. Moreover, being a system of regulating rotation by an engaging action of the key portion 1327b and the recess 515c, the structure is simple and does not require a complicated job at the time of installing for regulating the rotation. Even for preventing the round shaft 1327 from coming off, the handle 526 is simply to be turned, and therefore the job is simple.

Furthermore, structures as shown in FIG. 35 to FIG. 38 may be adopted. Although this installation mechanism 500' basically has a function similar to the abovementioned installation mechanism 500, a method of fixing to the guide rail 330 differs. Description of structures and functions similar to those of the installation mechanism 500 will be omitted to avoid repetition. In other words, it is method of installing the installation mechanism 500 by sliding from an end-portion side of the guide rail 330, and not installing on the guide rail 330 from above.

Figure 37:
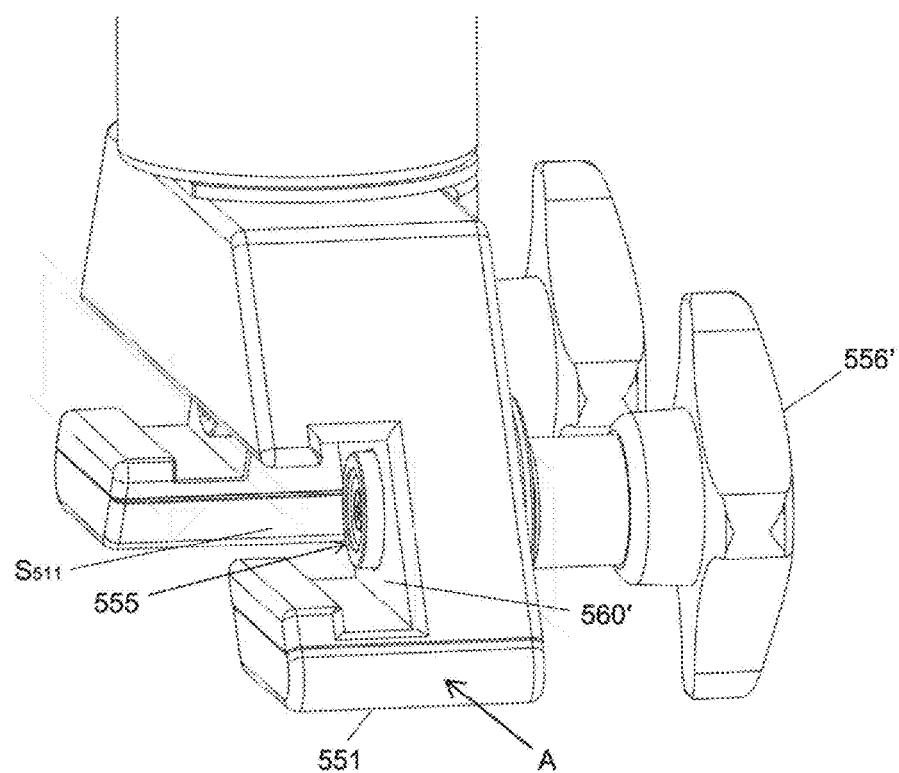
FIG. 37 is a perspective view showing in detail the installation mechanism in FIG. 35.
Figure 38:
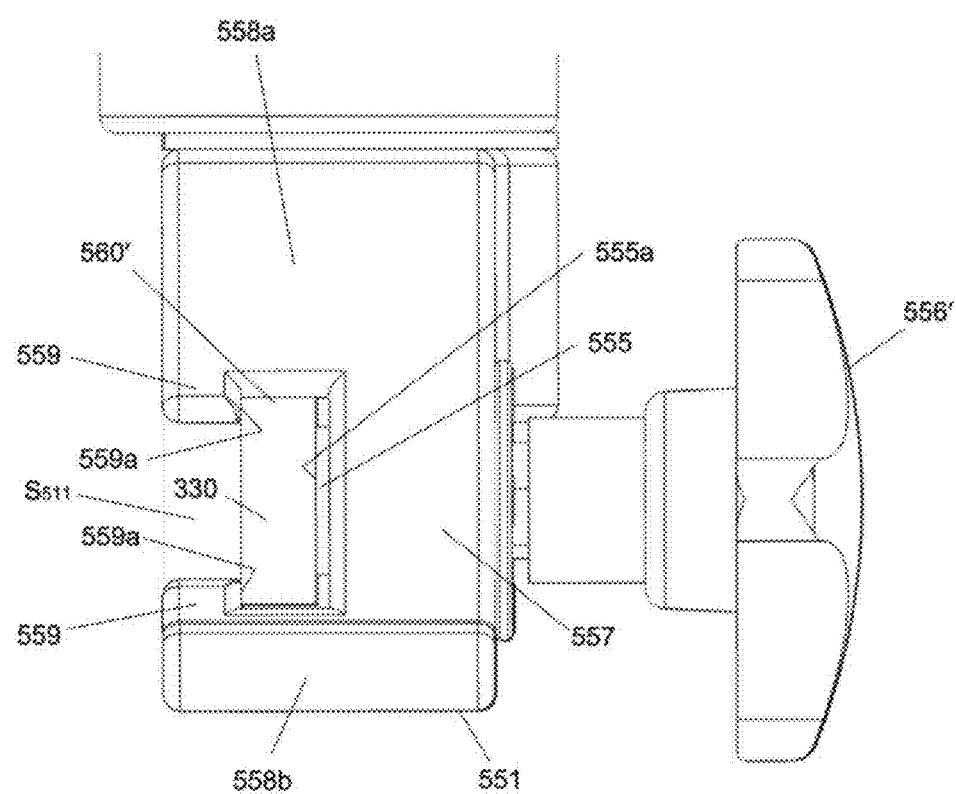
FIG. 38 is a diagram (viewed from a side-surface side) showing in detail the installation mechanism in FIG. 35.

As shown in FIG. 37 and FIG. 38, the extending portion 551 viewed from a direction of an arrow A is formed to be substantially U-shaped surrounding the guide rail. The 'substantial U-shape', as shown in FIG. 38, is formed by a first portion 557 facing one of side surfaces of the guide rail 330, a second portion 558a and a third portion 558b along an upper surface and a lower surface respectively of the guide rail 330, and a fourth portion 559 facing a side surface on an opposite side of the guide rail 330. More elaborately, as the fourth portion 559, a fourth portion 559 on an upper side making contact with an upper-surface side of the guide rail 330 and a fourth portion 559 on a lower side making contact with a lower-surface side of the guide rail 330 are formed. By such configuration, eventually, a cavity $S_{511}$ is formed as shown in FIG. 38. By making such configuration, it becomes possible to slide the installation mechanism 500 along the guide rail 330 without interfering with other member (not shown) installed on the guide rail 330.

In the example of FIG. 35 to FIG. 38, shapes of handles 526' and 556' differ from the aforementioned shapes, and it is possible to use various sizes and shapes for components of the installation mechanism 500. By turning the handle 556' and clamping both side surfaces of the guide rail 330 by a flat contact surface 555a of the abutting member 555 and a flat surface 559a of the fourth portion 559, a stable fixing of the installation mechanism 500 to the guide rail 330 is realized.

(4) Supplement to Explanation of Functions of Chemical Liquid Injector

A chemical liquid injector for angiography according to an aspect of the present invention may execute automatic injection by an 'infusion mode'. In a case of angiography, generally, the automatic injection of a chemical liquid is carried out only while a physician is pressing a predetermined switch of a chemical liquid injector. However, in the 'infusion mode', automatic injection of a chemical liquid is carried out over a predetermined time with an injection rate and/or an injection volume set in advance. The chemical-liquid in this case includes for example, an anticancer agent and the like. In this mode, the injection rate is set to a relatively low rate. The injection rate is 1.3 mL/sec in an example in FIG. 39. As the infusion mode, images as in FIG. 39A to 39D may be displayed.

Figure 39A:
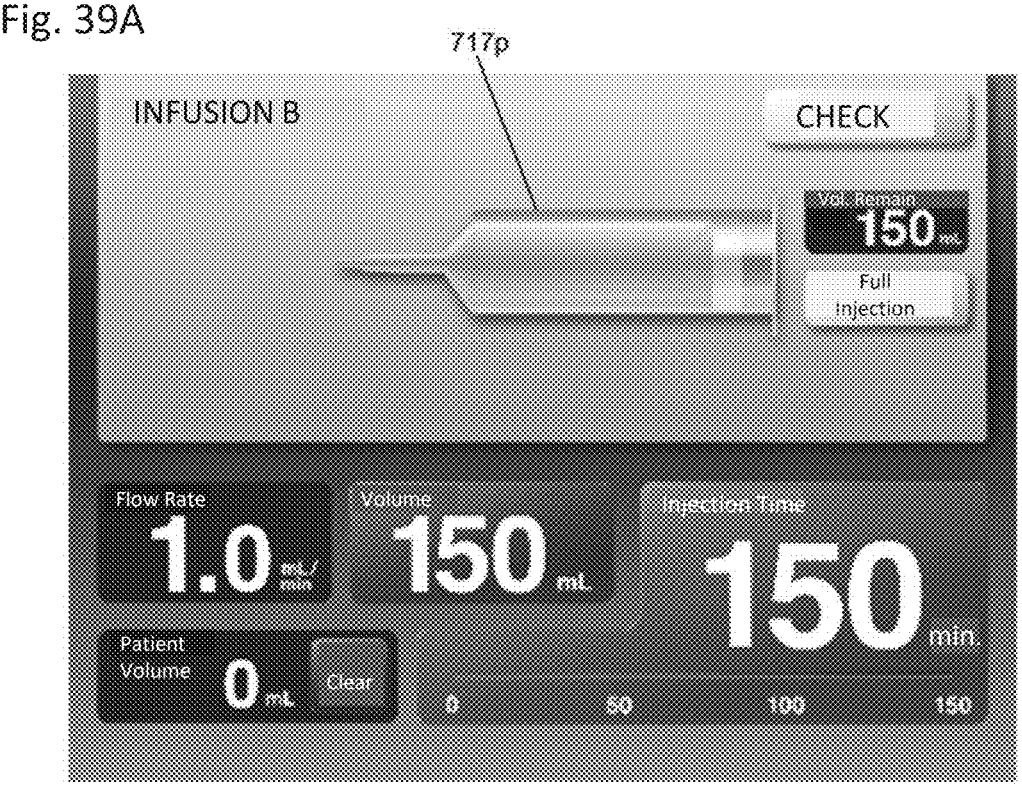
FIG. 39A is an example of a screen (a checking state) of an infusion mode.

FIG. 39A is a screen of a checking state. In this screen, an image 717p of syringe, a remaining volume of syringe, a full dosage injection button, an injection rate, an injection volume, an injection time, information of total volume are displayed. One or a plurality of these may be omitted. When a 'check button' on this screen is pressed, next, there is a transition to a standby state of FIG. 39B. Note that, an arrangement may be made such that, in these states, when a home button (not shown) is pressed, it is possible to return to a home screen (a screen from which various modes can be selected, and it is possible to shift to a selected mode).

Figure 39B:
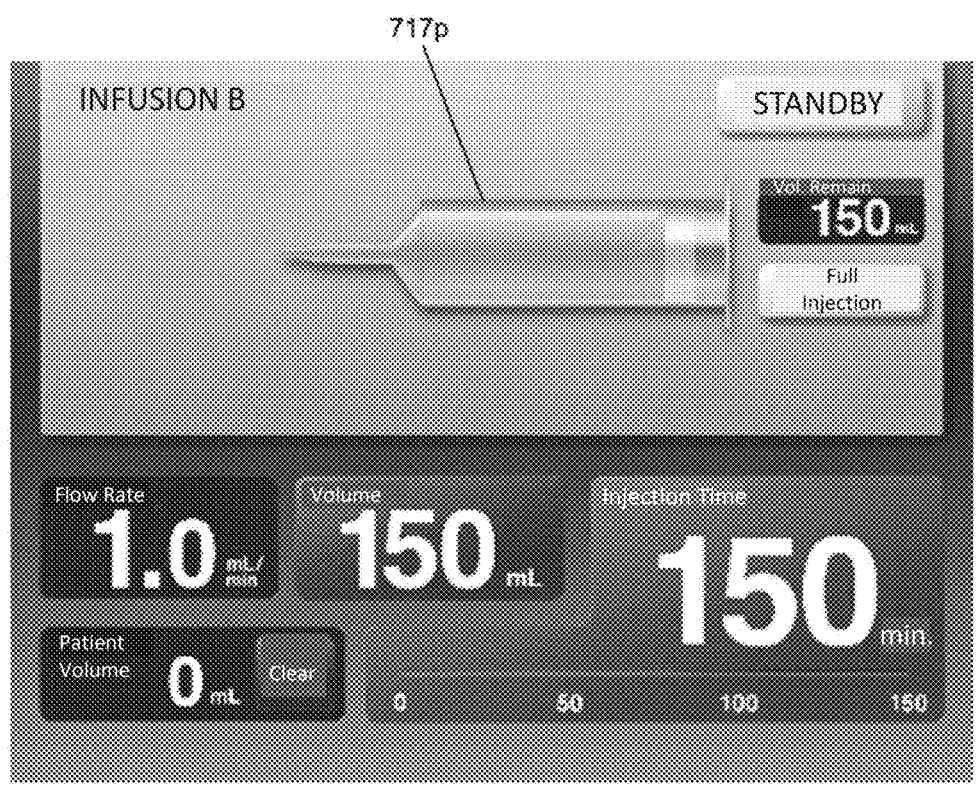
FIG. 39B is an example of a screen (the standby state) of the infusion mode.
Figure 39C:
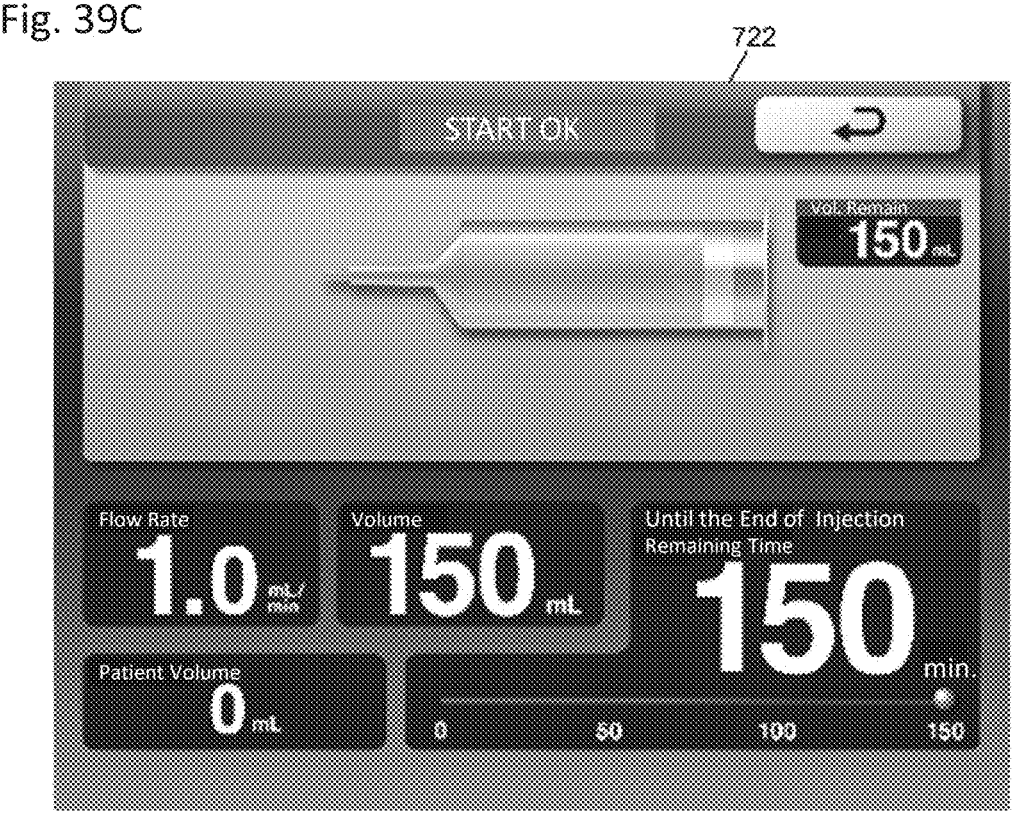
FIG. 39C is an example of a screen (the start-OK state) of the infusion mode.

When a 'standby button' is pressed on the screen of FIG. 39B, next, there is a transition to a standby state of FIG. 39C. In this screen, buttons switched to letters 'start OK' and a display for injection start for example, are displayed. Moreover, by pressing a button 722, or, by pressing other predetermined button, automatic injection in the infusion mode is started.

Figure 39D:
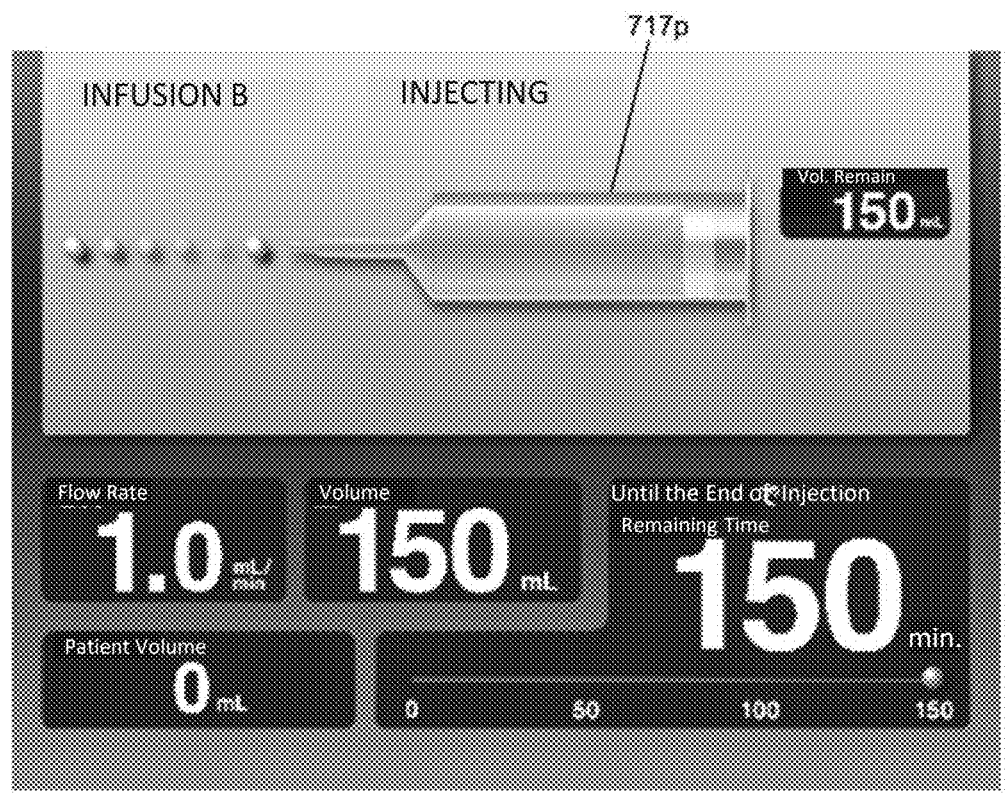
FIG. 39D is an example of a screen (injection-ON) of the infusion mode.

During injection, a screen as in FIG. 39D may be displayed. In this injection-ON screen, an animation display of a plurality of droplets being delivered from one syringe 717p is made. For a medical staff to be able to confirm that it is the infusion mode, a color of a chemical liquid in the syringe and/a color of liquid droplets may be displayed by colors different from those in the injection screen at the time of normal injection for angiography. For example, in the normal injection, the contrast medium may be displayed by green color and the physiological saline may be displayed by blue color, and in the infusion mode, the chemical liquids may be displayed by other colors. Regarding the injection time, the time remained may be displayed in a countdown form, or an indicator which can be checked visually may be displayed.

Note that, the infusion mode, basically, may be a mode in which the injection is continued till all the chemical liquid in the syringe is finished, and can be discontinued or stopped in mid-course if needed.

(5) CT Mode Injection by Chemical Liquid Injector for Angiography

The injection head of the chemical liquid injector for angiography as shown in FIG. 18 carries out injection at a high pressure (for example, 500 psi to 1200 psi) as it is necessary to inject a contrast medium through a thin catheter. However, a 'CT mode' of carrying out an injection of a relatively high pressure as executed by an injection head for CT examination, may be provided. In a chemical-liquid injection of the CT mode, the injection is executed in a range of 300 psi and lower than 300 psi for example. Moreover, an upper limit value (not more than 10 ml/sec for example) of the injection rate differing from that in angiography may be set. Although it is not limited, it may be configured such that it is possible to select via a graphical user interface, in which mode (here, the angiography mode and the CT mode) the chemical-liquid injection is executed. For instance, an icon indicating each mode may be displayed on the console screen, and a mode may be selected by the operator selecting any of those icons.

Thus, as in the injection in the angiography mode (angiography) and the injection in the CT mode, when the injection of different modes is possible, the chemical-liquid injection in each mode may be started by a common input operation, and the present embodiment may be configured as follows. In other words, an input for the injection-start in a certain mode and an input for the injection-start in another mode are set to be different operations. Specifically, for carrying out the injection in the angiography mode, it is necessary to press the hand switch for example, and for carrying out the injection in the CT mode, it is necessary to press a predetermined switch of another instrument. Since different inputs are necessary in such manner, execution of even safer chemical-liquid injection becomes possible.

Even when the chemical liquid injector 100 is communicably connected to the imaging apparatus 300-2 for angiography, it is preferable in one aspect that both instruments operate in synchronization. For instance, it may be configured to start the injection of the chemical liquid injector 100 when a predetermined instrument of the imaging apparatus 300-2 is operated. An image (such as an icon) indicating that the synchronization is ON, may be displayed on a predetermined display device of the chemical liquid injector. An image (such as an icon) indicating that it is in ON state when the screen has shifted to the standby screen, may be displayed. For instance, when a disconnected state is assumed due to a cable coming off unexpectedly, the following operation may be carried out.

in a case of a disconnected state assumed in the standby state, release standby, if the injection is ON, discontinue the injection.

(6) Light Emission Pattern

Figure 40:
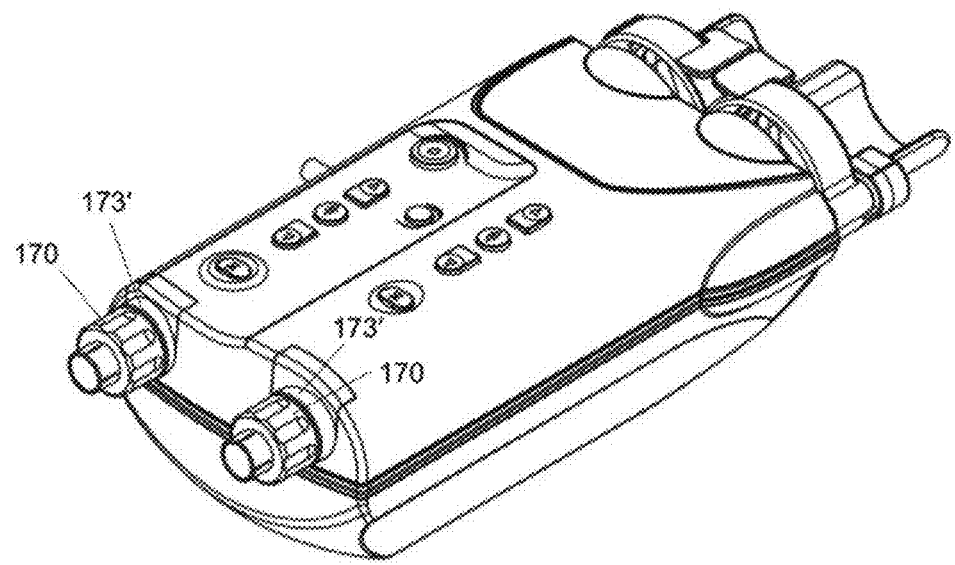
FIG. 40 is a perspective view showing an example in which an indicator portion, which is a light emitting portion of the injection head, has been changed.

Regarding the operation of the injection head 110, when the operation knob 170 (see FIG. 40) is rotated, or, in accordance with an operation situation of the piston driving mechanism, a light emitting portion 173' may emit light with a predetermined light pattern. Various patterns can be adopted as an arrangement pattern of light emitting elements of the light emitting portion 173', and here, a plurality of light emitting elements is arranged surrounding the operation knob 170 as in FIG. 41.

Figure 41:
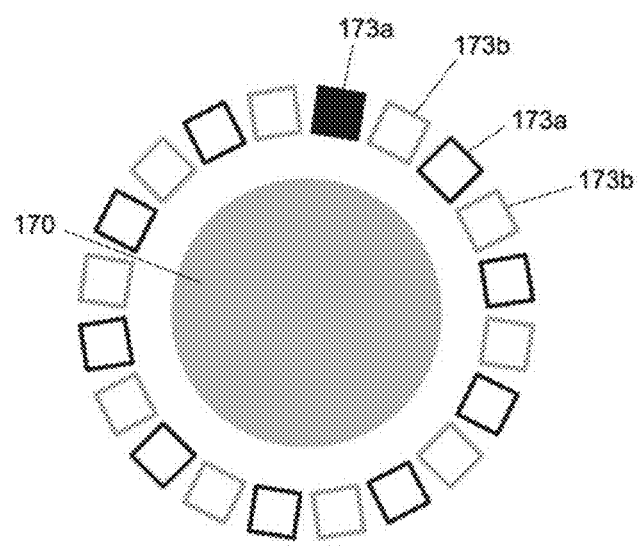
FIG. 41 is a diagram for explaining a light emission pattern.

As a light emitting element, light emitting elements capable of emitting light of a plurality of types of colors from one light emitting element may be arranged side-by-side, or, elements of different light emitting color may be arranged side-by-side alternately, or may be arranged side-by-side in a predetermined order. In FIG. 41, for indicating the difference in colors schematically, first color 173a and a second color 173b are shown.

The injection head 110 may be configured to perform an animation display in which the first color 173a is displayed sequentially in a clockwise direction or a counterclockwise direction when the ram member of the piston driving mechanism (at the time of chemical-liquid injection, when the operation knob is operated manually) is advanced. In this case, light of the second color 173b is not emitted. In a case in which the operation knob is being operated manually, a speed of the animation display (that is, a speed of switching the light emitting state of the light emitting element) may be changed in accordance with a speed of rotation. At the time of backing off the ram member, display in a direction opposite to the abovementioned direction is to be carried out. In case of automatic injection, the speed of the animation display (that is, a speed of switching the light emitting state of the light emitting element) may be changed in accordance with a light emitting state of the light emitting element.

It is preferable to have an arrangement such that the current status of the chemical liquid injector is revealed according to the light emitting pattern of the light emitting portion 173'. Therefore, in an embodiment of the present invention, if the 'start-OK' state has been assumed, the subsequent display may be made.

For one of the two light emitting portions 173' of the injection head 110, the light emitting element is to be turned on with the first color (for example, green color) corresponding to the first syringe and the other light emitting portion 173' is to be turned on with the second color (for example, light blue color) corresponding to the second syringe.

When an error state is assumed for some reason, the light emission pattern may be let to be such that one or both of the two light emitting portions 173' are turned on or blink repeatedly.

It is possible to combine each part having a technical characteristic disclosed in the present specification with other part having a technical characteristic. Moreover, also, of the plurality of components, it is possible to omit one or a plurality of components.

Note that, each of various components (such as a device, an apparatus, a means, a portion, and a unit) is not required to exist independently individually, and a plurality of components may be formed as one member. One component may be formed of a plurality of members. A certain component may be a part of another component. A portion of a certain component and a portion of another component may be same.

(Supplemental Notes)

The present application discloses the following invention. Note that, reference numerals in brackets are assigned for reference, and are not intended for limiting the present invention.

1. An injection head (110) comprising:
   a: a syringe holding unit (140) which holds a syringe in which a piston member is slidably inserted into a cylinder member having a circular cylindrical shape;
   b: a piston driving mechanism (130) having a ram member (131) for moving the piston member of the syringe; and
   c: a first light emitting portion (133a) which emits light with a first color and illuminates the syringe and a second light emitting portion (133b) which emits light with a second color and illuminates the syringe, wherein
      the first light emitting portion (133a) and the second light emitting portion (133b), viewed in a posture at the time of use of the injection head, are provided at an upper side of the ram member (131).

2. The first light emitting portion (133a) and the second light emitting portion (133b) are formed in a circular arc shape.

3. The first light emitting portion (133a) and the second light emitting portion (133b) have a circular arc shape coaxial with a central axis of the ram member.

4. The syringe is held by the syringe holding unit in a state of being accommodated in a protective case (840).
5. For light emission of the first light emitting portion (133a) and the second light emitting portion (133b), the injection head is configured to make such that,
   the first light emitting portion (133a) is not turned on or blinked in a preparation phase of a chemical-liquid injection, and
   the first light emitting portion (133b) is turned on or blinked in a chemical-liquid injection phase.
   The 'preparation phase' is a phase prior to reaching the chemical-liquid injection phase, and refers to a stage in which the syringe is set in the injection head, and a stage of filling a chemical liquid in the syringe.
   The 'chemical-liquid injection phase' may be only a stage in which a chemical liquid is injected practically, or, in addition to that, may include a stage immediately before that (for instance, a stage in which the operator carries out the final input (such as by pressing the 'start-OK' button for starting the injection) and/or a stage immediately after (a stage of the injection stop).
In such manner, by changing the mode of light emission in the preparation phase and the injection phase, the operator is able to know the phase at the current point of time.
6. The injection head is configured to turned on or blinked one or both of the first light emitting portion and the second light emitting portion when a syringe has been detected, or when the protective case mounted on the syringe has been detected, (transition from a light turned off state to the light turned on state).
7. The syringe holding unit has a clamper mechanism which holds a portion of the syringe or a portion of the protective case mounted on the syringe, and
   the injection head is configured to turn on or blink one or both of the first light emitting portion and the second light emitting portion when the clamper mechanism is switched from an open state to a closed state or from the closed state to the open state (transition from the light turned off state to the light turned on/blinked state).
8. A chemical liquid injector comprising:
an injection head (110) according to any of the above-mentioned; and
a console (210) which is connected to the injection head (110).
9. An injection condition setting system (210) comprising:
   one or a plurality of displays (146); and
   a control unit (250) which retains information of a graphic user interface for setting injection conditions in an apparatus which pushes out a chemical liquid from a first chemical-liquid storing body (800A) filled with a first chemical liquid and a second chemical-liquid storing body (800B) filled with a second chemical liquid, wherein
   the graphical user interface includes
   a display portion (716) which indicates information related to mixing conditions of the first chemical liquid and the second chemical liquid, and
   a window (715) for changing the mixing conditions, which includes an input button image (712) for an operator to input, and a plurality of mixing-method setting buttons (713) for selecting a method of mixing.
10. As the plurality of mixing-method setting buttons (713), at least two of a multiplying factor method button (713a), a percentage method button (713b), and a ratio method button (713c) are displayed.
11. The input button image (712) for the operator to input is a numerical keyboard (ten-key).
12. The first chemical-liquid storing body is a first syringe, and a second chemical-liquid storing body is a second syringe.

DESCRIPTION OF REFERENCE NUMERALS 100 chemical liquid injector
110 injection head
111 housing
111a front-end surface
130 piston driving mechanism
131 ram member
132 ball nut unit
133a, 133b (133), 133a', 133b' light emitting portion
135 ball screw
137 transmission mechanism
139 motor
139s rotation sensor
140 syringe holding unit
141 protective case support
145 clamper
146 display unit
150 control circuit
161 physical button
162 position sensor
163 clamper sensor
164 syringe sensor
165 pressure sensor
168 storage unit
169 interface
170 operation knob
173 indicator
190 power-supply unit
210 console
250 control unit
251 display
253 touch panel
257 slot
261 storage unit
262 communication unit
269 interface
300 (300-1, 300-2) imaging apparatus
330 guide rail
311 RIS
313 PACS
315 information management apparatus
317 information display terminal
319 monitor in imaging room
500 installation mechanism
510 holding assembly
515 receiving hole
526 handle
527 engaging member
550 base assembly
551A, 551B extending portion
555 abutting member
556, 556' handle
557, 558a, 558b, 559
first portion to fourth portion
560 receiving groove
701 human body image
703 imaging part
704a, 704b indicator 705*a* injection rate window
705*b* injection volume window
706*a*, 706*b*, 706*c* phase display portion
706*s*, 707*s* mixing device image
707*w* window
707~709 image button
711 image button
712 ten-key
713*a*~713*c* dilution setting button
714 enter key
715, 715' numerical keypad window
717*a*, 717*b*, 717*p* syringe
718 mixing device
719*a*, 719*b* path
721 temporary-stop display
722 image button
800 (800A, 800B) syringe
810 cylinder member
820 piston member (plunger)
840 protective case
1320 holding mechanism
1325 base portion
1327 round shaft
1331, 1337 arm member
1341 holding member
1705*a*, 1705*b* window
1761 injection result display
1762 mode display
1763 window

What is claimed is:

1. An injection condition setting system comprising:
one or a plurality of displays; and
a control unit which retains information of a graphical user interface for setting injection conditions in an apparatus which pushes out a chemical liquid from a first chemical-liquid storing body filled with a first chemical liquid and a second chemical-liquid storing body filled with a second chemical liquid; wherein
the graphical user interface includes
a display portion which indicates information related to mixing conditions of the first chemical liquid and the second chemical liquid, wherein the display portion includes an image that indicates that an injection is a mixed injection of the first chemical liquid and the second chemical liquid and functions as an image button, and
a window for changing the mixing conditions, wherein the window includes an input button image for an operator to input, and a plurality of mixing-method setting buttons for selecting a method of mixing,
wherein the control unit is configured to:
(a) display the window when the image is manipulated by a user; and
(b) display an image on a screen indicating that the injection is the mixed injection during the mixed injection.

2. The injection condition setting system according to claim 1, wherein as the plurality of mixing-method setting buttons, at least two of a multiplying factor method button, a percentage method button, and a ratio method button are displayed.

3. The injection condition setting system according to claim 1, wherein the input button image for the operator to input is a numerical keypad.

4. The injection condition setting system according to claim 1, wherein
the first chemical-liquid storing body is a first syringe, and
the second chemical-liquid storing body is a second syringe.

5. The injection condition setting system according to claim 1, wherein the images represent a mixing device used for mixing the first chemical liquid with the second chemical liquid in graphic form.

* * * * *